US010037684B1

(12) United States Patent
Garcia et al.

(10) Patent No.: US 10,037,684 B1
(45) Date of Patent: Jul. 31, 2018

(54) WATERPROOF NURSECALL PULLCORD STATION

(71) Applicant: Rauland-Borg Corporation, Mount Prospect, IL (US)

(72) Inventors: Reuben P. Garcia, Evanston, IL (US); Levi J. Perea, Jr., Chicago, IL (US); Steve Grabowski, Arlington Heights, IL (US); Dejan Zivancevic, Arlington Heights, IL (US)

(73) Assignee: Rauland-Borg Corporation, Mount Prospect, IL (US)

( * ) Notice: Subject to any disclaimer, the term of this patent is extended or adjusted under 35 U.S.C. 154(b) by 0 days.

(21) Appl. No.: 15/597,410

(22) Filed: May 17, 2017

(51) Int. Cl.
*G08B 25/12* (2006.01)
*A61B 5/00* (2006.01)

(52) U.S. Cl.
CPC ............ *G08B 25/12* (2013.01); *A61B 5/0022* (2013.01); *A61B 5/7465* (2013.01)

(58) Field of Classification Search
CPC ...... G08B 25/12; A61B 5/0022; A61B 5/7465
USPC .................................................... 340/286.07
See application file for complete search history.

(56) References Cited

U.S. PATENT DOCUMENTS

| | | | | | |
|---|---|---|---|---|---|
| 4,728,928 | A * | 3/1988 | Shipley | G08B 25/016 | 200/61.77 |
| 4,792,798 | A * | 12/1988 | Wilowski | A61F 4/00 | 340/286.07 |
| 2007/0035402 | A1* | 2/2007 | Dawson | G08B 25/016 | 340/573.1 |
| 2009/0264006 | A1* | 10/2009 | Silkey | H01R 12/716 | 439/350 |
| 2010/0109854 | A1* | 5/2010 | Varney | A61B 5/1115 | 340/286.06 |
| 2013/0300548 | A1* | 11/2013 | Robinson | G06F 19/327 | 340/286.07 |

* cited by examiner

*Primary Examiner* — Hirdepal Singh
(74) *Attorney, Agent, or Firm* — Leydig, Voit & Mayer, Ltd.

(57) ABSTRACT

Embodiments of the disclosure provide a waterproof pull-cord station for management of patient care. The pullcord station includes a cord, and a face plate assembly coupled to a wall plate assembly. The face plate assembly includes a cord retainer coupled to the cord, and an actuator post coupled to the cord retainer. The wall plate assembly includes a wall plate comprising a frontside and a backside, wherein the frontside comprises a single material and the backside comprises an opening, the wall plate serving as a housing for an electronic circuit. The wall plate assembly further includes the electronic circuit wirelessly coupled to the actuator post and configured to determine whether the cord has been pulled by monitoring the wireless coupling between the actuator post and the electronic circuit. The wall plate assembly further includes a back cap configured to interface with the opening of the backside.

21 Claims, 21 Drawing Sheets

WATERPROOF NURSECALL PULLCORD STATION

BACKGROUND

Hospitals, clinics, and other types of healthcare facilities are equipped with nurse call systems that utilize various devices located throughout the hospital. The nurse call systems enable patients and/or nurses to communicate over a network with one or more nurse stations. The nurse call system helps in organizing hospital resources and facilitating communication in the hospital environment so as to enhance patient safety and improve staff efficiency. Pullcord stations may be engineered to work with nurse call systems, allowing a call to be placed to the nurse call system by pulling a cord on the pullcord station. Pullcord stations are effective in enhancing the quality and care of a patient since a patient can place a priority call with a simple act.

SUMMARY

Embodiments of the disclosure provide a waterproof pullcord station for management of patient care, the pullcord station includes a cord, a face plate assembly, and a wall plate assembly. The face plate assembly includes a cord retainer coupled to the cord, and an actuator post coupled to the cord retainer. The wall plate assembly includes a wall plate comprising a frontside and a backside, wherein the frontside comprises a single material and the backside comprises an opening, the wall plate serving as a housing for an electronic circuit. The wall plate assembly further includes the electronic circuit wirelessly coupled to the actuator post and configured to determine whether the cord has been pulled by monitoring the wireless coupling between the actuator post and the electronic circuit. The wall plate assembly further includes a back cap configured to interface with the opening of the backside. The face plate assembly is coupled to the wall plate assembly.

Embodiments of the disclosure further provide a system for management of patient care. The system includes a nurse call server comprising a processor and a non-transitory computer readable medium; and a waterproof pullcord station. The waterproof pullcord station includes a cord, a face plate assembly, and a wall plate assembly coupled to the faceplate assembly. The face plate assembly includes a cord retainer coupled to the cord, and an actuator post coupled to the cord retainer. The wall plate assembly includes: a wall plate comprising a frontside and a backside, wherein the frontside comprises a single material and the backside comprises an opening, the wall plate serving as a housing for an electronic circuit. The wallplate assembly further includes the electronic circuit wirelessly coupled to the actuator post and configured to determine whether the cord has been pulled by monitoring the wireless coupling between the actuator post and the electronic circuit. The wall plate assembly further includes a back cap configured to interface with the opening of the backside. The waterproof pullcord station initiates a call to the nurse call server when the cord has been pulled.

Embodiments of the disclosure further provide a waterproof pullcord station. The pullcord station includes a cord, a face plate assembly, and a wall plate assembly coupled to the face plate assembly. The face plate assembly includes a cord retainer coupled to the cord, and an actuator post coupled to the cord retainer. The wall plate assembly includes a wall plate comprising a frontside and a backside, wherein the frontside comprises a single material and the backside comprises an opening. The wall plate assembly further includes a back cap configured to interface with the opening of the backside to seal the backside creating an interior cavity with the backside; wherein the face plate assembly is configured to allow excess liquid to drain from the pullcord station, and the wall plate assembly is configured to prevent ingress of water in the interior cavity.

BRIEF DESCRIPTION OF THE SEVERAL VIEWS OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Healthcare providers that manage multiple patients with a limited number of staff members utilize nurse call systems to facilitate communication between the staff and patients. The nurse call system not only serves to enhance communication between staff and patients, but it also improves communication among staff members. For example, a nurse attending to a patient in a hospital room may register his or her location using a device that interfaces with the nurse call system. In so doing, other staff members of the hospital know the location of the nurse when they view visual indicators on nurse call devices such as corridor lights. Several devices may interface with nurse call systems, for example, a pillow speaker, a pullcord station, corridor lights, staff terminals, etc. The capabilities and functionalities of these devices range from performing complex tasks like making phone calls to simple tasks like turning on an alarm.

Pullcord stations are important to healthcare providers, for example, hospitals, because they can quickly provide a patient an avenue to alert hospital staff or staff members at a healthcare facility when a patient needs help. Embodiments of the disclosure provide pullcord stations that may interface with a networked computing system, for example, a nurse call system, in a healthcare facility. The pullcord stations are further designed to be accessible in wet locations, such as, showers and bathrooms. Since pullcord stations include electronic components for interfacing with, for example, a nurse call system in a healthcare facility, the pullcord stations in the disclosure are waterproof.

Ingress Protection (IP) ratings are used to specify the degree of protection provided by enclosures against intrusion of foreign objects/materials and water. Ingress Protection ratings and requirements are specified in IEC standard 60529. Since pullcord stations mounted in bathrooms or other wet areas are susceptible to damage or malfunction due to water ingress, the waterproofing of the pullcord station is expected to hold up to prevent damage due to water, steam, or liquid ingress. Normal operation of the stations is expected to be maintained when exposed to water or high humidity.

Figure 1:
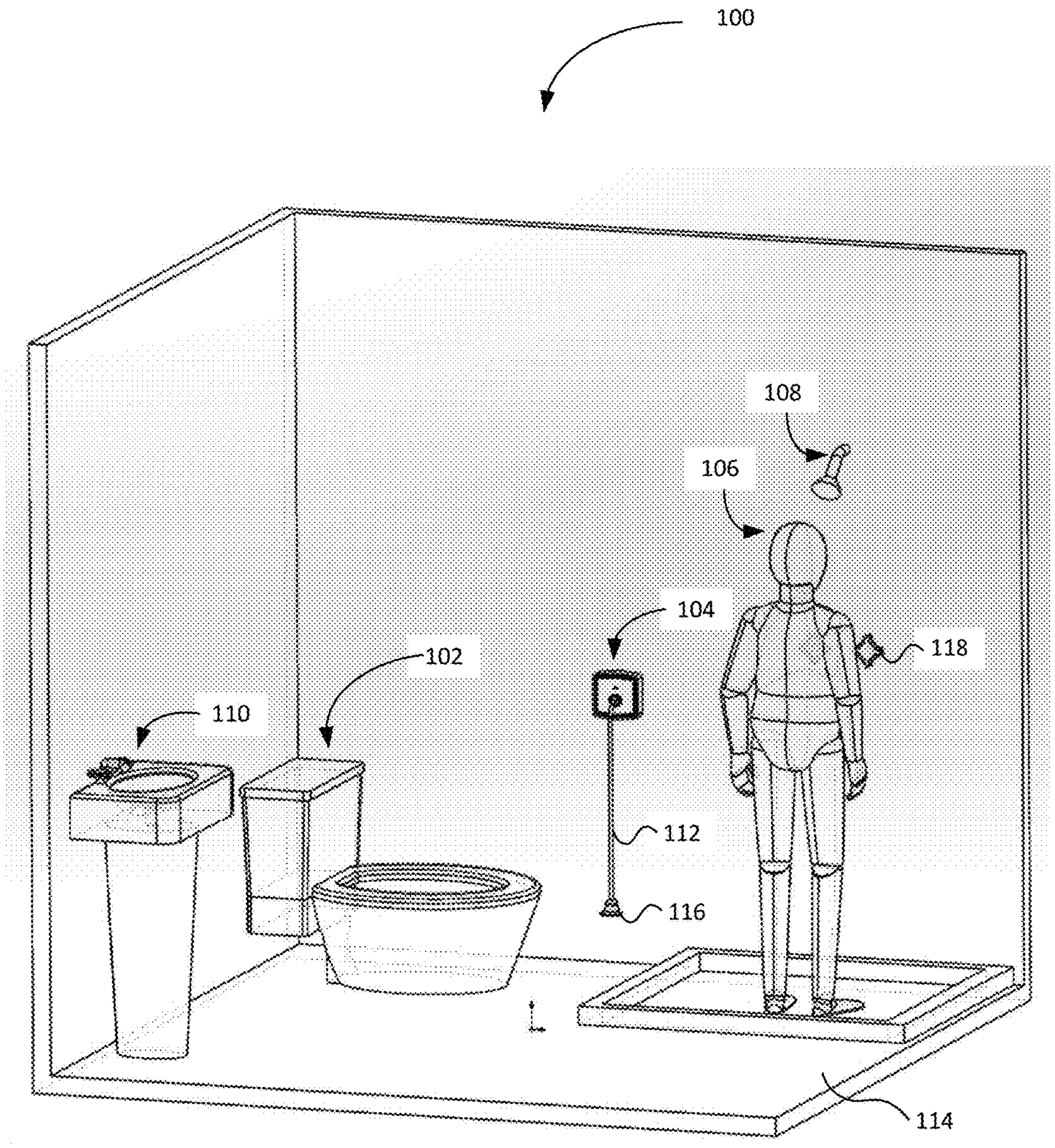
FIG. 1 provides an example environment showing a pullcord station installed in a bathroom setting.

FIG. 1 illustrates an example setup of a bathroom 100 showing an installation of a pullcord station 104. The bathroom 100 includes a bathroom sink 110, a toilet 102, the pullcord station 104, a showerhead 108, and dials 118 to operate the showerhead 108. A patient 106 is shown standing in the shower area of the bathroom 100 in order to provide a reference for an installed height of the pullcord station 104. The pullcord station 104 includes a cord 112 and a weighted portion 116. The pullcord station 104 is installed in a manner so that the cord 112 is for example at least 3 feet long and the weighted portion 116 which may be a bell or tear-dropped shape is within 3 inches of the bathroom floor 114.

In the environment illustrated in FIG. 1, the pullcord station 104 is installed close to the toilet 102 so that when the patient 106 is on the toilet 102, the patient 106 has access to the cord 112. The pullcord station 104 is also installed in a manner such that the station 104 is accessible to a patient using the shower area. For example, if the patient 106 falls on the bathroom floor 114, then the patient 106 has access to either the weighted portion 116 or the cord 112 of the pullcord station 104. FIG. 1 shows the pullcord station 104 installed in the bathroom 100, but it is understood that the pullcord station 104 can be installed at other locations throughout a healthcare facility. The bathroom 100 is only shown as an example. After the cord 112 on the pullcord station 104 is pulled, the pullcord station 104 sends a signal to an emergency alert system for the healthcare facility. The emergency alert system informs healthcare facility staff that the cord 112 of pullcord station 104 is pulled.

Figure 2:
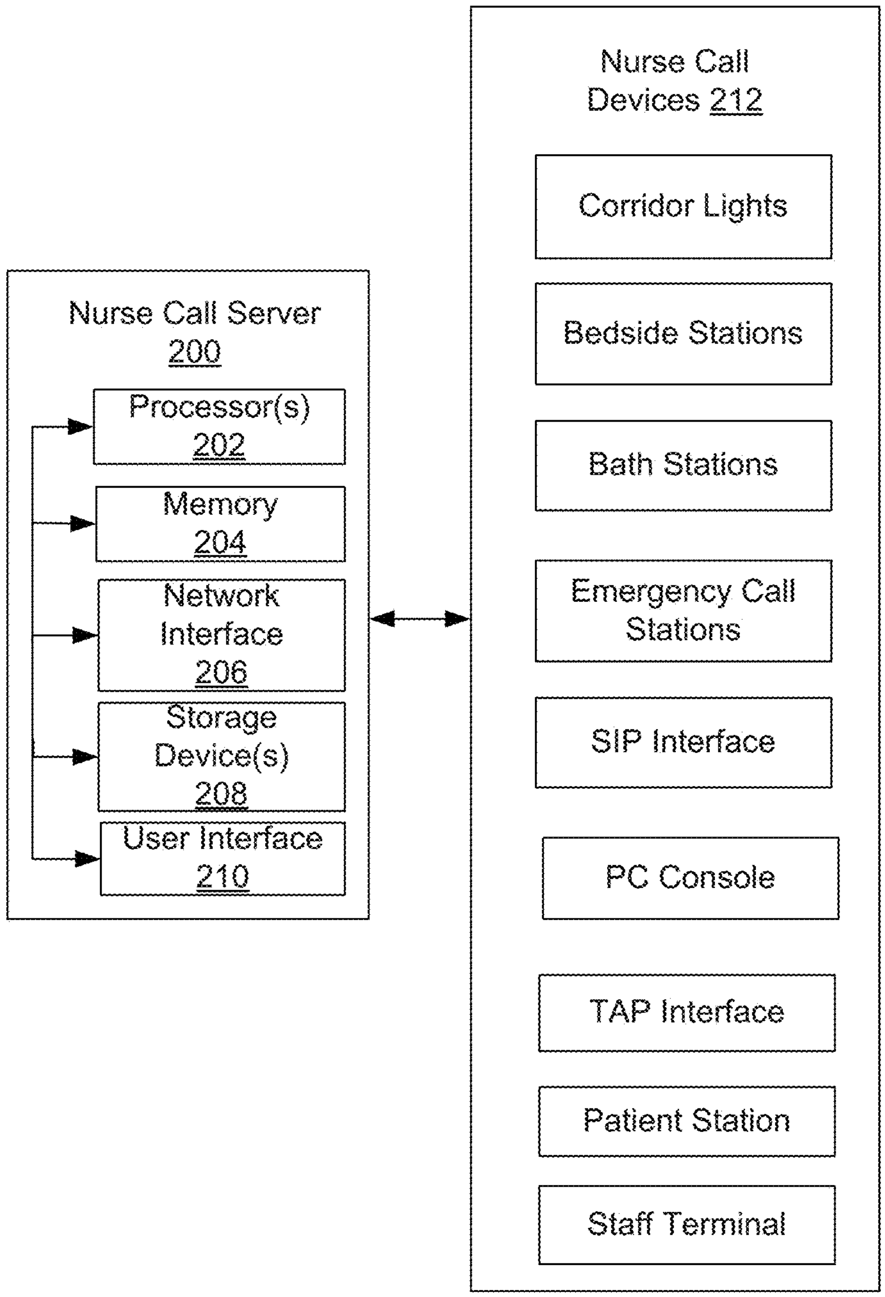
FIG. 2 provides a sample block diagram identifying several components in a nurse call system.

The pullcord station 104 interfaces with an emergency alert system of a healthcare facility and may be part of a larger group of nurse call devices in a healthcare facility. FIG. 2 provides a sample block diagram identifying several components in the nurse call system according to some embodiments of the disclosure. In the embodiment illustrated in FIG. 2, the nurse call system includes a nurse call server 200 coupled to nurse call devices 212. The nurse call server 200 may be communicably coupled to the nurse call devices 212 over a nurse call network.

The nurse call server 200 includes one or more processors 202, memory 204, network interface 206, storage devices 208, and user interface 210. To simplify the discussion, the singular form will be used for all components identified in the nurse call server 200 when appropriate, but the use of the singular does not limit the discussion to only one of each component. For example, multiple processors may implement functionality attributed to processor 202.

Processor 202 is configured to implement functions and/or process instructions for execution within the nurse call server 200. For example, processor 202 executes instructions stored in memory 204 or instructions stored on the storage device 208. In certain embodiments, instructions stored on storage device 208 are transferred to memory 204 for execution at processor 202. Memory 204, which may be a non-transient, computer-readable storage medium, is configured to store information within the nurse call server 200 during operation. In some embodiments, memory 204 includes a temporary memory that does not retain information stored when power to the nurse call server 200 is lost. Examples of such temporary memory include volatile memories such as random access memories (RAM), dynamic random access memories (DRAM), and static random access memories (SRAM). Memory 204 also maintains program instructions for execution by the processor 202 and serves as a conduit for other storage devices (internal or external) coupled to the nurse call server 200 to gain access to processor 202.

Storage device 208 includes one or more non-transient computer-readable storage media. Storage device 208 is provided to store larger amounts of information than memory 204, and in some instances, configured for long-term storage of information. In some embodiments, the storage device 208 includes non-volatile storage elements. Non-limiting examples of non-volatile storage elements include floppy discs, flash memories, magnetic hard discs, optical discs, solid state drives, or forms of electrically programmable memories (EPROM) or electrically erasable and programmable (EEPROM) memories.

Network interface 206 is used to communicate with external devices and/or servers. The nurse call server 200 may comprise multiple network interfaces 206 to facilitate communication via multiple types of networks. Network interfaces 206 may comprise network interface cards, such as Ethernet cards, optical transceivers, radio frequency transceivers, or any other type of device that can send and receive information. Non-limiting examples of network interfaces 206 include radios compatible with several Wi-Fi standards, 3G, 4G, Long-Term Evolution (LTE), Bluetooth®, etc.

The nurse call server 200 may include one or more user interfaces 210. User interfaces 210 may be separated into input devices and output devices. Output devices are configured to provide output to a user using tactile, audio, and/or video information. Input devices are configured to receive input from a user or an input sensor. Examples of output devices may include a display screen (cathode ray tube (CRT) display, liquid crystal display (LCD) display, LCD/light emitting diode (LED) display, organic LED display, etc.), a sound card, a video graphics adapter card, speakers, magnetics, or any other type of device that may generate an output intelligible to user. Examples of input devices may include a presence-sensitive screen or a touch-sensitive screen, a mouse, a keyboard, a video camera, microphone, a voice responsive system, or any other type of input device.

A host of nurse call devices 212 may be connected to the nurse call server 200. Nurse call devices 212 include corridor lights, bedside stations, bath stations, emergency call stations, SIP interface, PC consoles, TAP interface, patient station, and staff terminal. The architecture in FIG. 2 allows for connection of pullcord station 104 to the nurse call server 200 since bedside stations, bath stations, emergency call stations, and so on may be implemented as pullcord stations.

Figure 3:
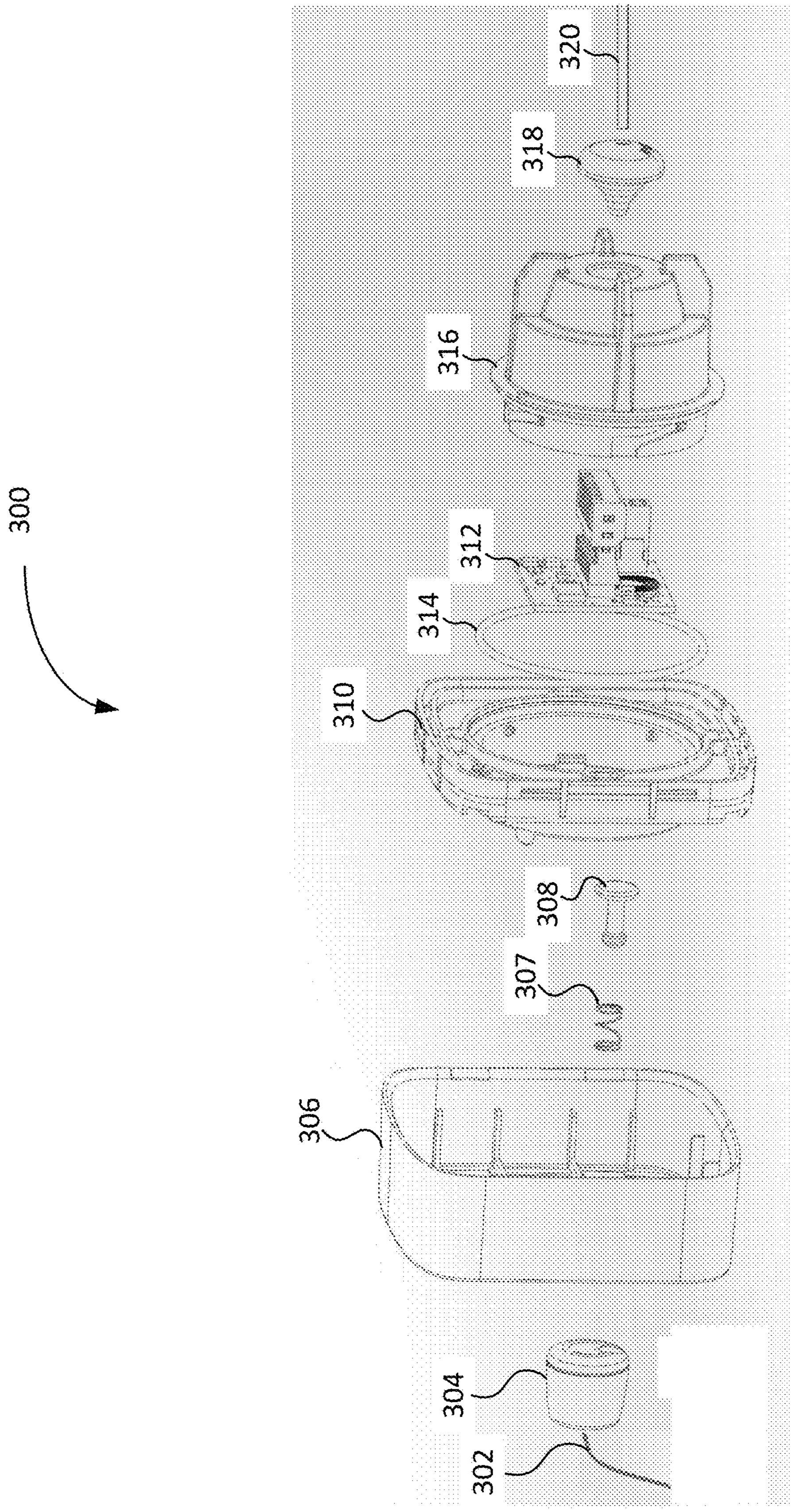
FIG. 3 illustrates several components of a pullcord station in accordance with an embodiment of the disclosure.

FIG. 3 illustrates several components of a waterproof pullcord station 300 in accordance with an embodiment of the disclosure. The waterproof pullcord station 300 may include a cord 302 coupled to a cord retainer 304. The cord retainer 304 is secured to the face plate 306 with an actuator post 308, and a spring 307 is provided to hold the actuator post 308 in a preferred direction. The face plate 306 serves as a cosmetic face of the pullcord station 300, covering the wall plate 310. The wall plate 310 includes an opening for housing a circuit board 312. The waterproof pullcord station 300 then includes an O-ring 314 or a toric joint and a back cap 316. The back cap 316 includes an opening to receive a cable grommet 318. The cable grommet 318 includes an opening to receive an electric cable 320.

The cord 302 may be pulled by a patient or an enduser for signaling to a nurse for help. The cord 302 may be extruded, for example, a polyvinyl chloride (PVC) exterior with interior reinforcing strands, with smooth, slippery bacterial-resisting exteriors. The cord 302 may also be made from woven strands of material, for example, nylon, cotton, etc. The cord retainer 304 retains the cord 302 and attaches to the actuator post 308. The face plate 306 provides an opening for the actuator post 308 to pass through to interface with the cord retainer 304. The cord retainer 304 includes an opening that interfaces with one extreme of the actuator post 308, allowing the cord retainer 304 to pivot so that a call can be actuated when the cord is pulled perpendicular to the wall plane in any direction, parallel to the wall plane in any direction, or in an intermediate direction between the perpendicular and parallel directions. The rounded bottom (half-toroid) of the cord retainer 304 provides a smooth action of the actuator to place a call when the cord is pulled from any direction. The cord retainer 304 acts like a lever that operates in 360° to move or pry the actuator post 308 when there is a side-force applied to the actuator post 308 by the cord retainer 304 in response to the cord being pulled in some direction. The actuator post 308 includes a metalized, flat surface that is inductively coupled to a sensor on the circuit board 312 and used for activating the call signal to the nurse.

The wall plate 310 provides holes for mounting the waterproof pullcord station 300 to a wall. The wall plate 310 has an opening on its backside for accepting and mounting the circuit board 312. Also on the backside, the wall plate 310 has a round channel for sealing to an O-ring 314. The wall plate 310 also includes one or more debossed pins for locking to the back cap 316. The backside of the wall plate 310 faces the wall that the waterproof pullcord station 300 is mounted, and in some instances, the back cap 316 protrudes into the wall.

The circuit board 312 includes an inductive sensing switch for sensing the inductive target on the flat surface of the actuator post 308. The inductive target may be realized by making the flat surface of the actuator post 308 a conductive or a metalized surface. The inductive sensing switch may be a Texas Instrument® inductive sensing switch. The circuit board 312 further provides an electrical connection point to a central computer system, for example, the nurse call server 200. The circuit board 312 may include in addition to the wired interface with the electric cable 320 a wireless communication interface.

The O-ring 314 provides a sealing function when compressed between the wall plate 310 and the back cap 316 at the time of installation. The O-ring 314 may be manufactured with different materials that may be compressed while providing a sealing function, for example, silicone, nitrile rubber (buna-N), and ethylene propylene diene monomer (EPDM) rubber. The back cap 316 includes a round channel for sealing to the O-ring 314. The sealing function provided by the O-ring 314 prevents water and other fluids from entering the pullcord station 300 through the interface between the wall plate 310 and the back cap 316. The back cap 316 may also include a number of embossed channels for locking to the wall plate 310, for example, four embossed channels. The back cap 316 may be made from plastic. The back cap 316 may further include an opening for receiving the cable grommet 318, for example, an IP-67 cable grommet.

The cable grommet 318 has a pass through opening for sealing to a category type electrical cable. The cable grommet 318 fits snugly to an opening in the back cap 316 and provides a sealing function for the electric cable 320. The sealing function provided by the cable grommet 318 prevents water or other fluids from entering the pullcord station 300 through the opening on the back cap 316 that receives the cable grommet 318.

Figure 4B:
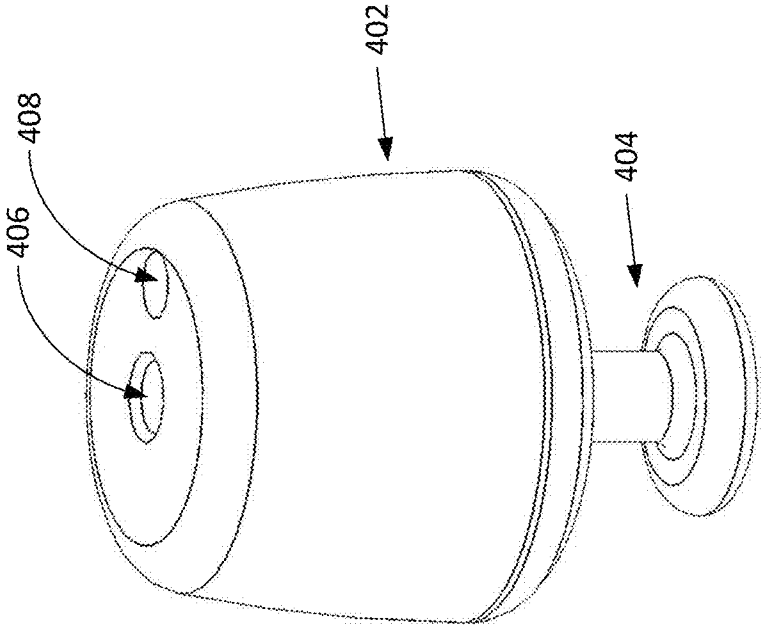
FIGS. 4A-4B illustrate an actuator post and a cord retainer according to an embodiment of the disclosure.
Figure 4A:
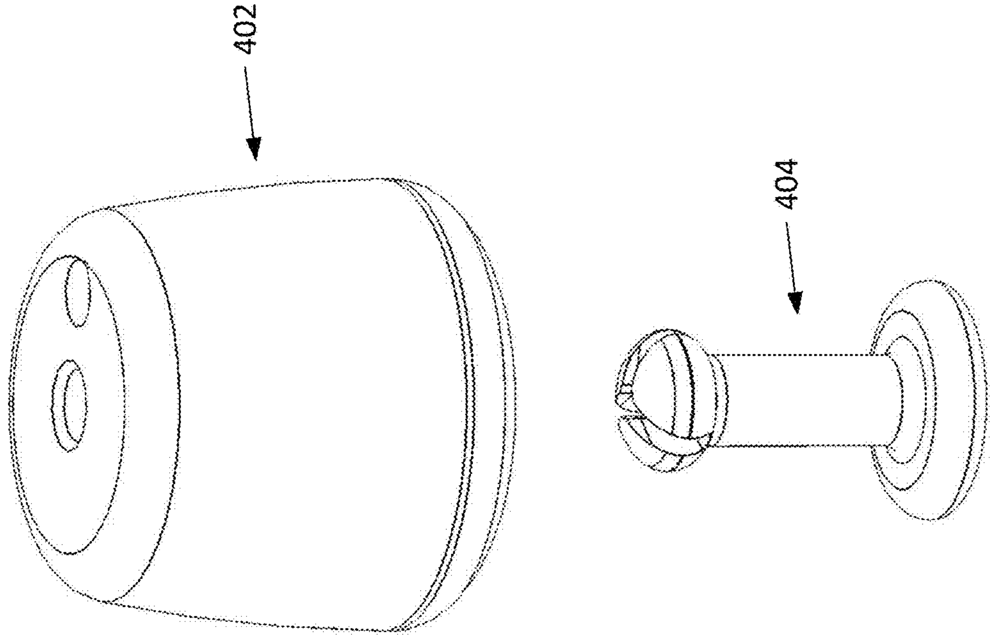

FIGS. 4A-4B illustrate an actuator post 404 and a cord retainer 402 according to an embodiment of the disclosure. The actuator post 404 is shown in FIG. 4A separate from the cord retainer 402, and is shown interfacing with the cord retainer 402 in FIG. 4B. The configuration of FIG. 4B shows how the cord retainer 402 would lock in with the actuator post 404 when installed with the face plate (not shown). The cord retainer 402 includes two openings, a first opening 406 and a second opening 408, for receiving a cord (not shown) of the pullcord station.

Figure 4C:
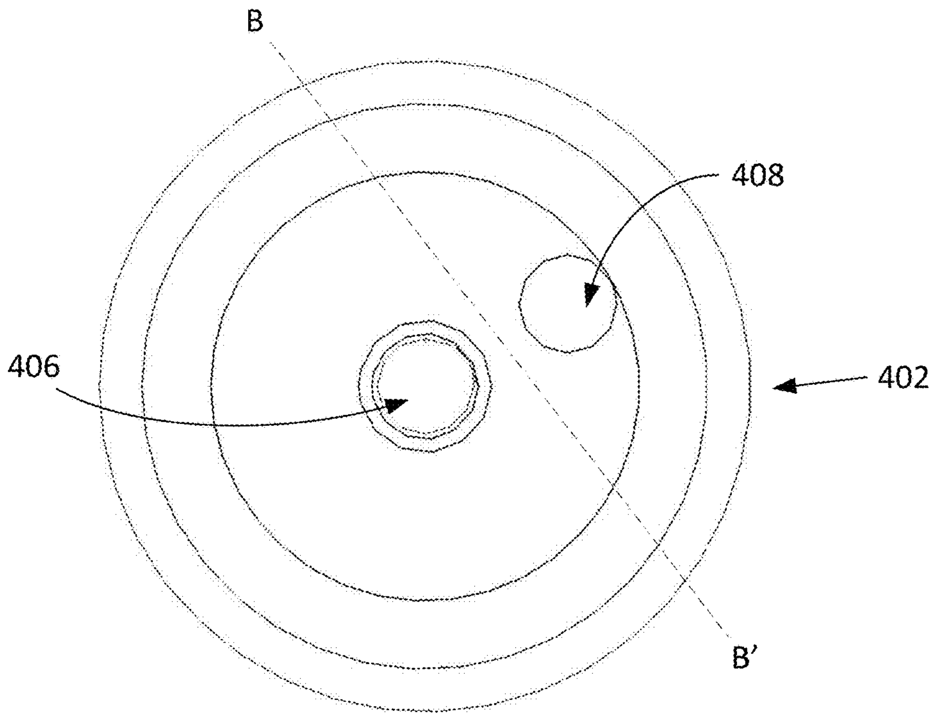
FIGS. 4C-4F illustrate various section views of the cord retainer in FIG. 4A according to an embodiment of the disclosure.
Figure 4D:
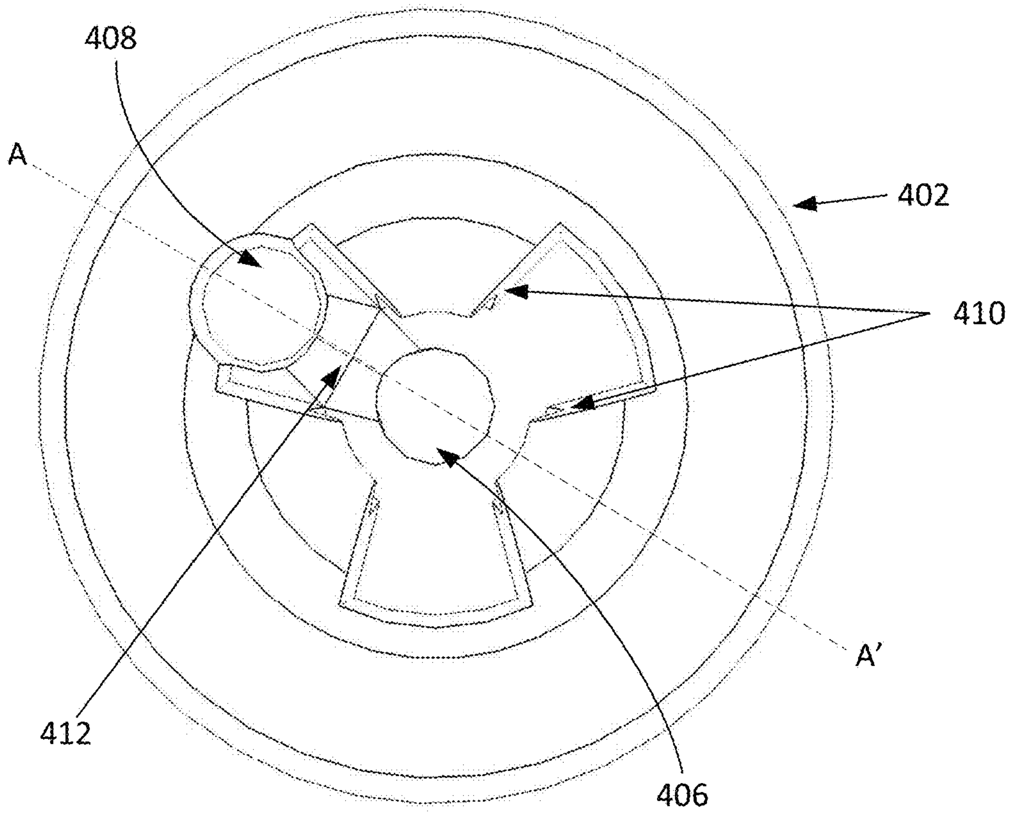

FIGS. 4C-4F illustrate various section views of the cord retainer 402 in FIG. 4A according to an embodiment of the disclosure. FIG. 4C shows a top view of the cord retainer 402, depicting the two openings 406 and 408. FIG. 4D shows a bottom view of the cord retainer 402. The cord retainer 402 is shown to have radial surface portions 410 that are engineered to hold an actuator post in place. The actuator post would be prevented from easily sliding out by the hanging of the radial surface portions 410 of the cord retainer 402. The cord retainer 402 is also shown to include a high friction region 412. The high friction region 412 is engineered to hold a cord (not shown) of a pullcord station in place by preventing the cord from sliding out through one of the openings 406 or 408. During cord installation, one end of the cord is fit though the top of the cord retainer 402 through the first opening 406, then wrapped around the high friction region 412 and fit through the second opening 408 from the bottom of the cord retainer 402. In some embodiments, the cord is installed before installing the actuator post 404. FIGS. 4C and 4D include guided markings B-B' and A-A', respectively, which are related to the perspective section views in FIGS. 4E and 4F.

Figure 4E:
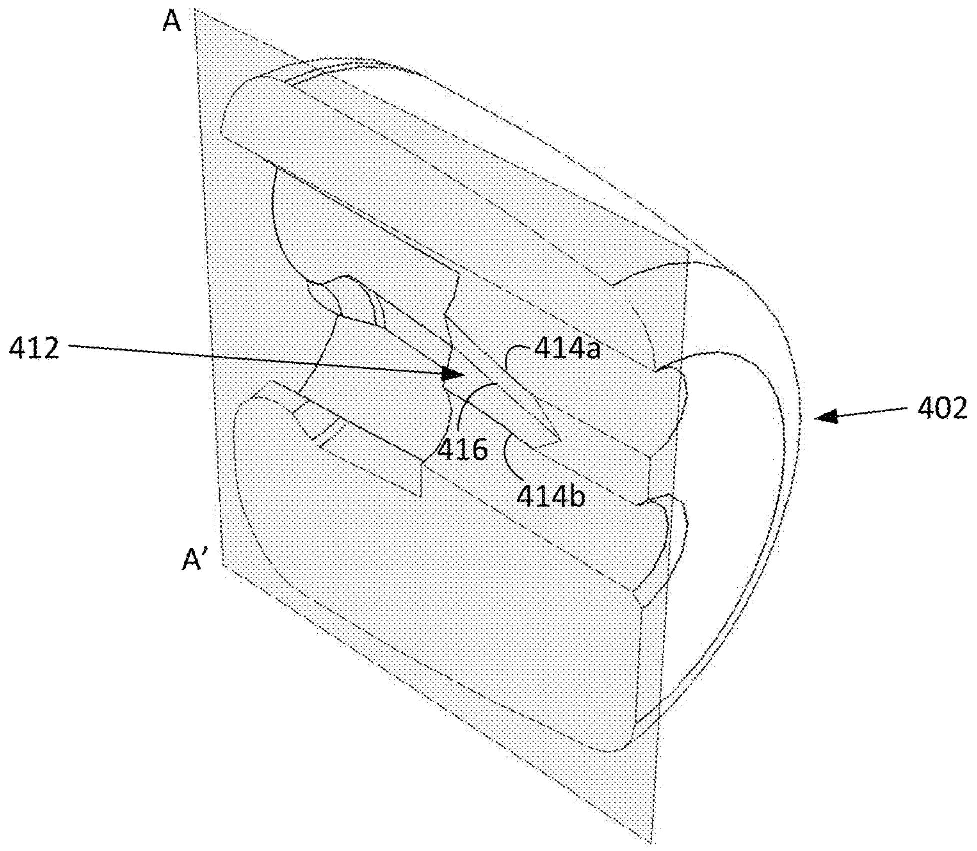
Figure 4F:
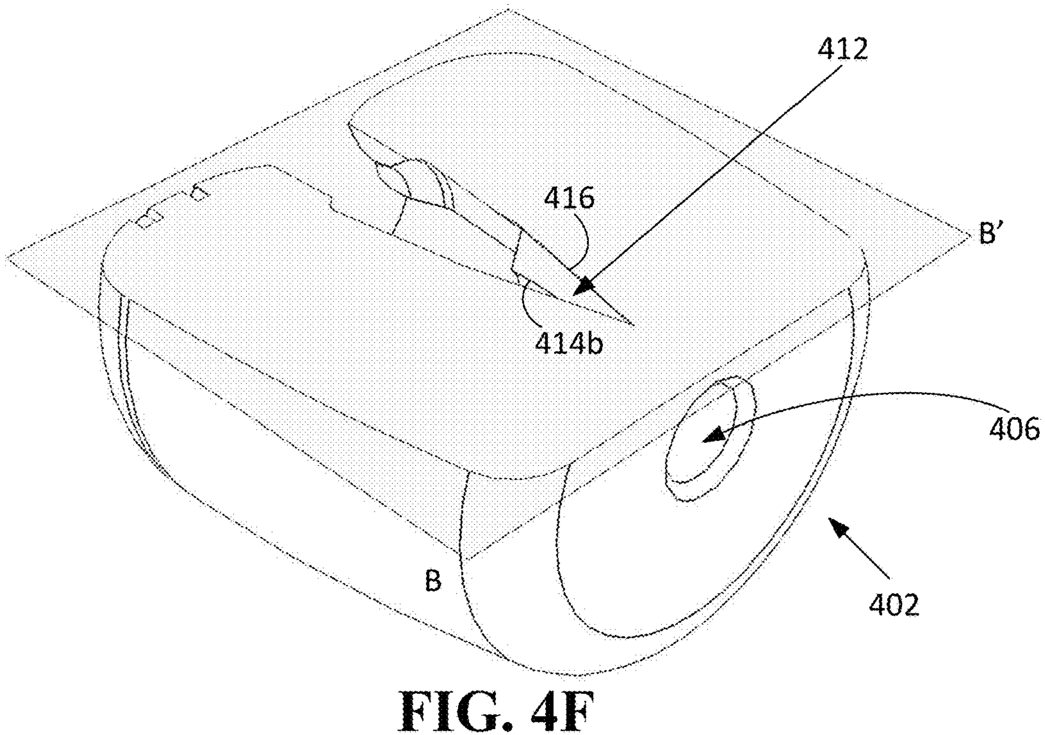

FIGS. 4E and 4F further illustrate one embodiment of the high friction region 412. In FIG. 4F, the high friction region 412 is shown to have a sharp 'V' cross section. The sharp 'V' cross section allows cords of different diameter to fit snugly and not slide out of either of the openings 406 and 408. FIG. 4E shows that the high friction region 412 may include a recessed gradation 416. FIG. 4E also shows two side gradations 414*a* and 414*b* that form two sharp 'V' shapes with their counterparts (not shown). A cord installed in the cord retainer 402 would fit snugly at the sharp 'V' shapes of 414*a* and its counterpart and 414*b* and its counterpart. These two sharp 'V' shapes serve as two stopping points when the cord is installed snugly in the cord retainer 402.

The cord retainer 402 serves to retain or hold the cord in place. When installing the cord to the cord retainer 402, tool termination, tying a knot, and fasteners are not required. The 'V' shape in the middle allows for the cord to sit in place without sliding back and forth. As the cord is used over time and due to cord stretching and/or wear and tear, it's diameter changes, and the 'V' shape allows the cord to slip further down into the 'V' formed by the 'V' shape.

The 'V' shape cavity of the cord retainer 402 allows for a progressive lock of a cord which might be of varying diameter and might also be constructed of material which, when under loads applied by pull forces, deforms and varies its diameter. By allowing for a progressive locking function, the V-shape cavity ensures that a smaller diameter cord will simply be pulled deeper in to the 'V' rather than pulling though openings 406 and 408 and becoming unlocked.

In some embodiments, the cord retainer 402 is provisioned with more than two openings 406 and 408. The more than two openings allows for providing additional friction when an installed cord is pulled. The plurality of openings on the cord retainer 402 will allow the cord to be woven through from one opening to another.

In some embodiments, the cord retainer 402 is not provisioned with a high friction area but other means of attaching the cord to the cord retainer 402 are used. For example, the cord may be guided through opening 406 and out opening 408, and a knot may be tied to prevent the cord from slipping out of the cord retainer through opening 408 and then through opening 406. In another embodiment, the cord may be guided through opening 406 and a knot is tied so as to prevent the cord from slipping out of the cord retainer through the opening 406. In another embodiment, a washer is provided such that the cord is affixed to the washer and the washer has an outer diameter that prevents the washer from passing through the opening 406. In another embodiment, a zip tie may be used to attach the cord to the cord retainer.

The cord retainer 402 is able to lock (and unlock) with an actuator post without requiring an installer to use a tool or disassemble the pullcord station of the cord retainer 402. In one embodiment, the cord retainer 402 and the actuator post have a compression fit where the head of the actuator post compresses to pass into the opening 406 from the bottom of the cord retainer 402. Then once inside the inner cavity of the cord retainer 402, the head of the actuator post expands to provide a locking mechanism, preventing the two pieces (the actuator post and the cord retainer 402) from being separated. The two pieces remain unseparated until enough force is applied to once more sufficiently compress the head of the actuator post to allow it to pass though the opening 406 from the bottom of the cord retainer 402. When the head of the actuator post expands inside the inner cavity of the cord retainer 402, the radial surface portions 410 prevent the expanded head of the actuator post to separate from the cord retainer 402. When compressed, the head of the actuator post can pass through the opening 406 from the bottom of the cord retainer 402, but when expanded, the head of the actuator post cannot pass through the opening 406 from the bottom of the cord retainer 402 because of the radial surface portions 410.

Figure 5A:
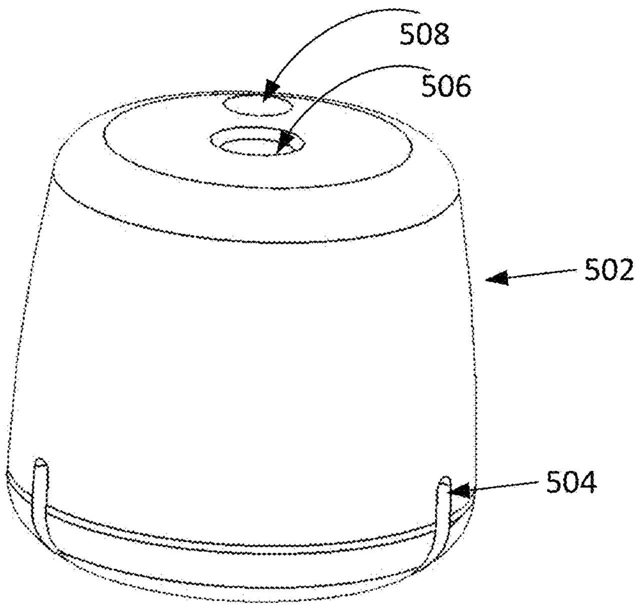
FIG. 5A illustrates another cord retainer according to an embodiment of the disclosure.

FIG. 5A illustrates another cord retainer 502 that may be used in a pullcord station according to an embodiment of the disclosure. The cord retainer 502 includes two openings, a first opening 506 and a second opening 508, for receiving a cord (not shown) of the pullcord station. The cord retainer 502 further includes one or more channels 504. The one or more channels 504 are expansion cuts that provide pressure relief during installation and removal of an actuator post that interfaces with the cord retainer 502. These expansion cuts or relief cuts allow for flex of the cord retainer 502.

Figure 5B:
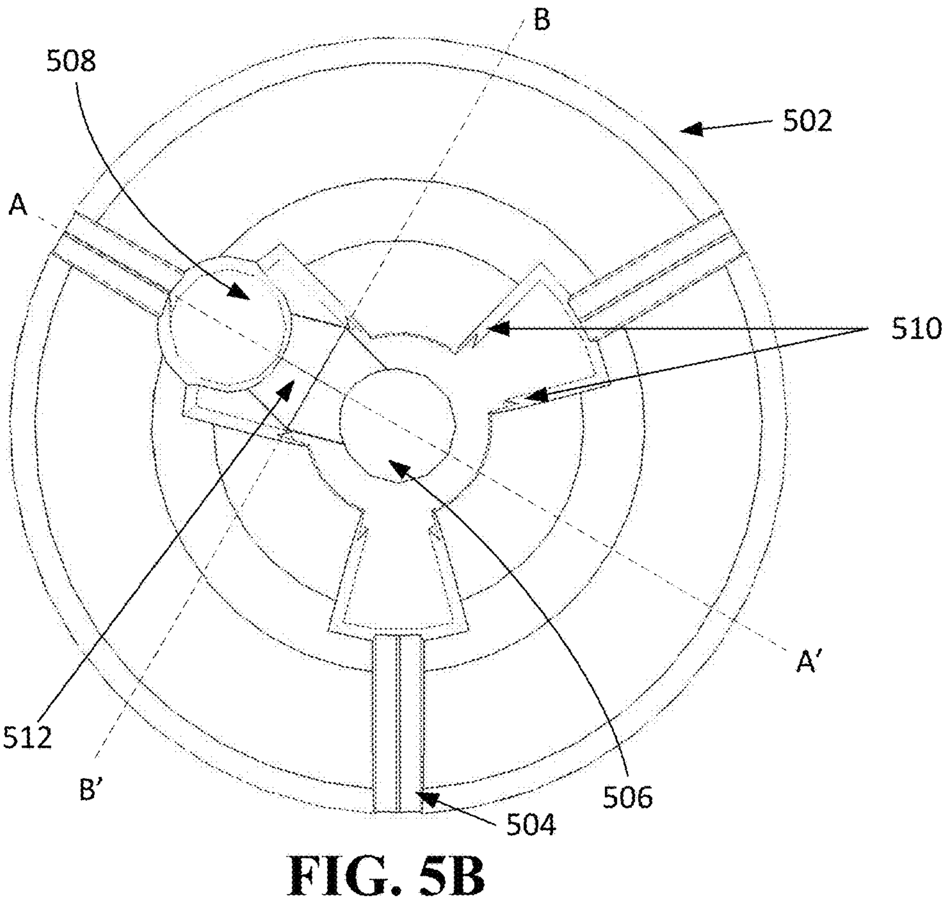
FIGS. 5B-5D illustrate various section views of the cord retainer in FIG. 5A according to an embodiment of the disclosure.
Figure 5C:
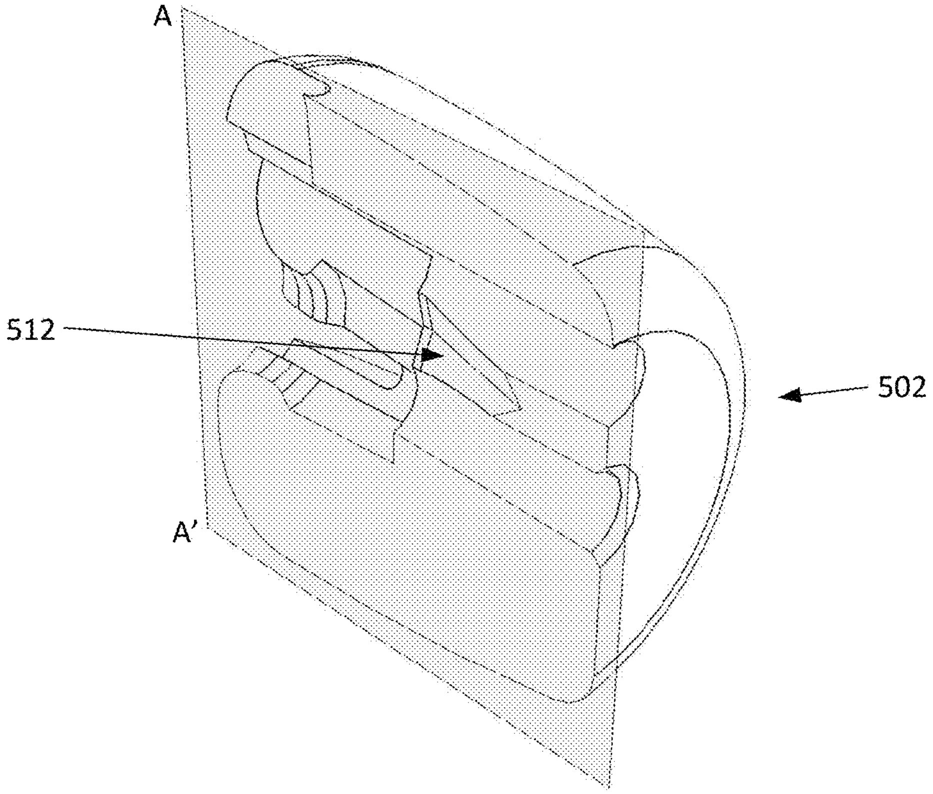
Figure 5D:
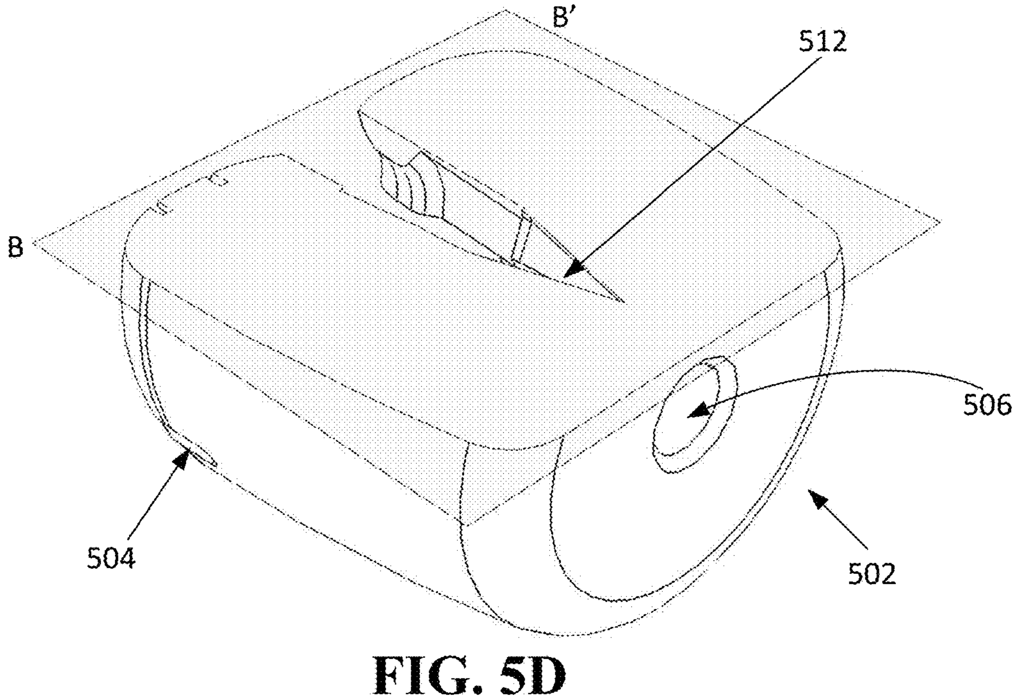

FIG. 5B illustrates a bottom view of the cord retainer 502, showing the two openings 506 and 508, the channels 504, retainer radial surface portions 510, and a high friction region 512. The high friction region 512 is similar to that of FIG. 4D and the description is similar to high friction region 412. FIGS. 5C-5D further illustrate the nature of the high friction region 512.

Figure 6A:
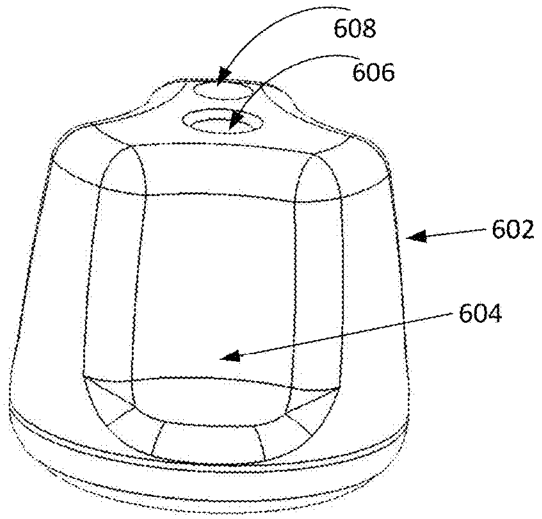
FIG. 6A illustrates yet another cord retainer according to an embodiment of the disclosure.
Figure 6B:
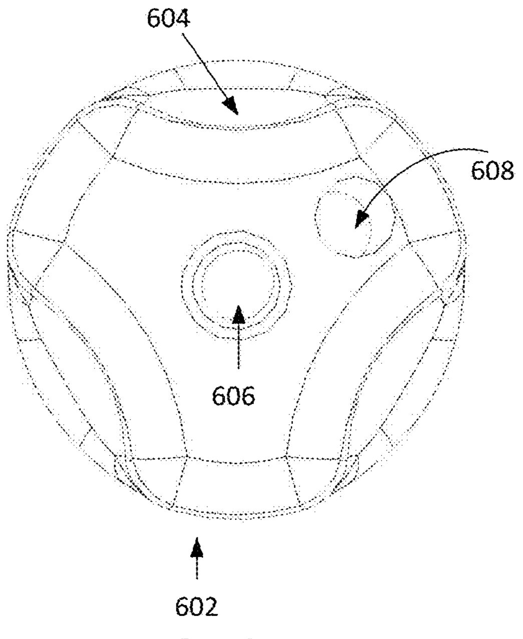
FIGS. 6B-6C illustrate various section views of the cord retainer in FIG. 6A according to an embodiment of the disclosure.
Figure 6C:
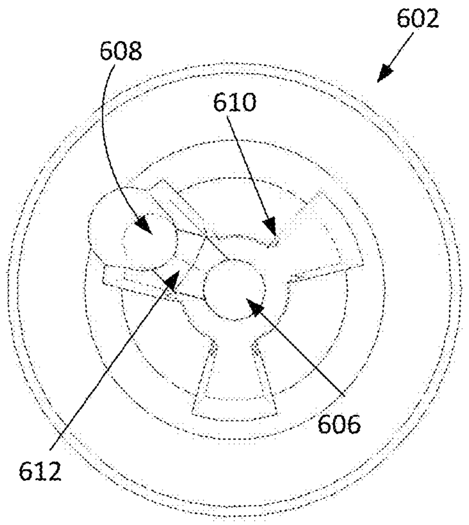

FIG. 6A illustrates another cord retainer 602 for a pullcord station according to an embodiment of the disclosure. The body of the cord retainer 602 includes one or more contours 604. The contour 604 provides an easier grip of the cord retainer 602 during installation, servicing, and uninstallation of the pullcord station. As in previous embodiments, the cord retainer 602 includes two openings 606 and 608 for receiving a cord (not shown). FIG. 6B illustrates a top view of the cord retainer 602, and FIG. 6C illustrates a bottom view of the cord retainer 602. The cord retainer has a high friction region 612, for holding the cord in place, and radial surface portions 610, for holding an actuator post in place.

The cord retainer 602 is able to lock (and unlock) with an actuator post without requiring an installer to use a tool or disassemble the pullcord station of the cord retainer 602. The cord retainer 602 has the opening 608 on the bottom of the cord retainer 602 which allows the actuator post to first enter the inner cavity of the cord retainer 602 from the bottom into an unlocked outside position. The actuator post then slides past a region of high friction, which the shaft of the actuator post must pass though, before reaching the center of the inner cavity of the cord retainer 602. This center region includes the radial surface portions 610 designed to allow the actuator post to snap into and out of the inner cavity of the cord retainer 602. Once seated in the center region in the inner cavity of the cord retainer 602, the actuator post is locked into place with the cord retainer 602.

Figure 7B:
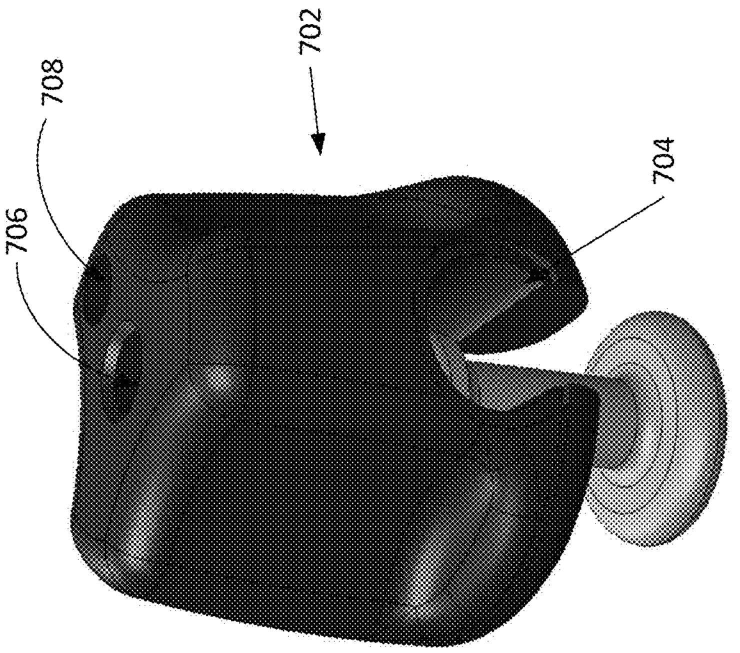
FIGS. 7A-7B illustrate an actuator post and a cord retainer according to an embodiment of the disclosure.
Figure 7A:
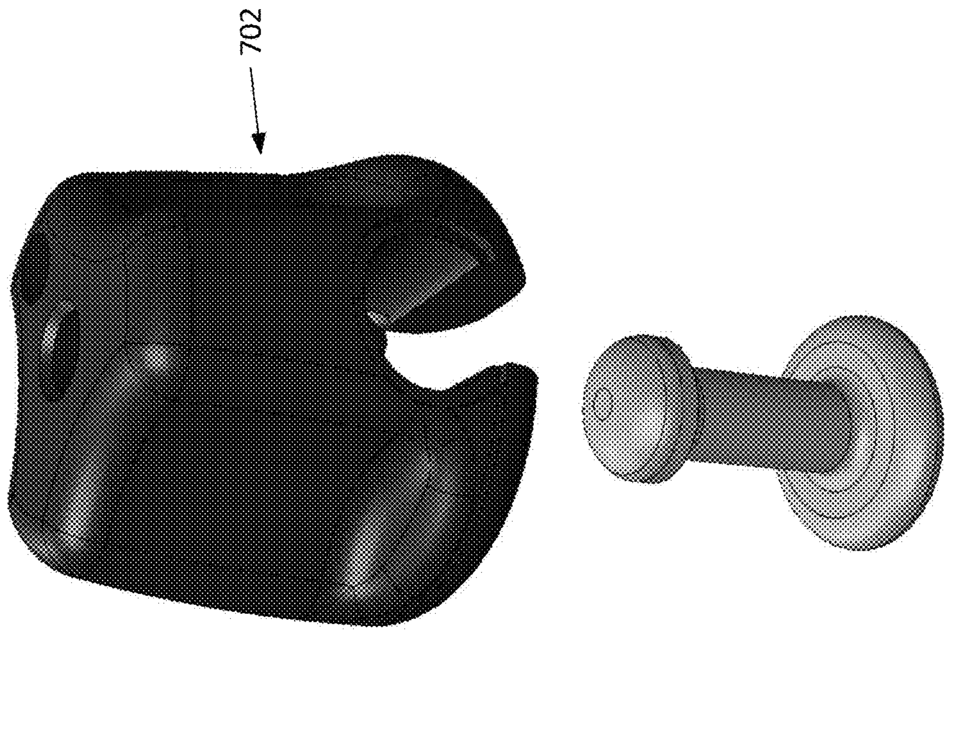

FIGS. 7A and 7B illustrate an actuator post and a cord retainer 702 according to an embodiment of the disclosure. The actuator post is shown in FIG. 7A separate from the cord retainer 702, and is shown interfacing with the cord retainer 702 in FIG. 7B. The configuration of FIG. 7B shows how the cord retainer 702 would lock in with the actuator post when installed with the face plate (not shown). The cord retainer 702 includes two openings, a first opening 706 and a second opening 708, for receiving a cord (not shown) of the pullcord station. The cord retainer 702 provides a port 704 for sliding the actuator post in place.

The cord retainer 702 is able to lock (and unlock) with an actuator post without requiring an installer to use a tool or disassemble the pullcord station of the cord retainer 702. The cord retainer 702 includes an opening (the port 704) on the side of the cord retainer 702 which allows the actuator post to pass laterally into the inner cavity of the cord retainer 702 without compressing the head of the actuator post. In some embodiments, an element of the inner cavity of the cord retainer 702 which prevents the actuator post from sliding out of the port 704 is a region of high friction which the shaft of the actuator post must pass though before reaching the center of the inner cavity of the cord retainer 702. This region is designed to allow the actuator post to snap into and out of the center of the inner cavity of the cord retainer 702. Once seated in the center of the cavity of the cord retainer 702, the actuator post is locked into place with the cord retainer 702. This design allows the cord retainer 702 to transmit pull forces without unlocking or disconnecting from the attached actuator post.

Figure 8A:
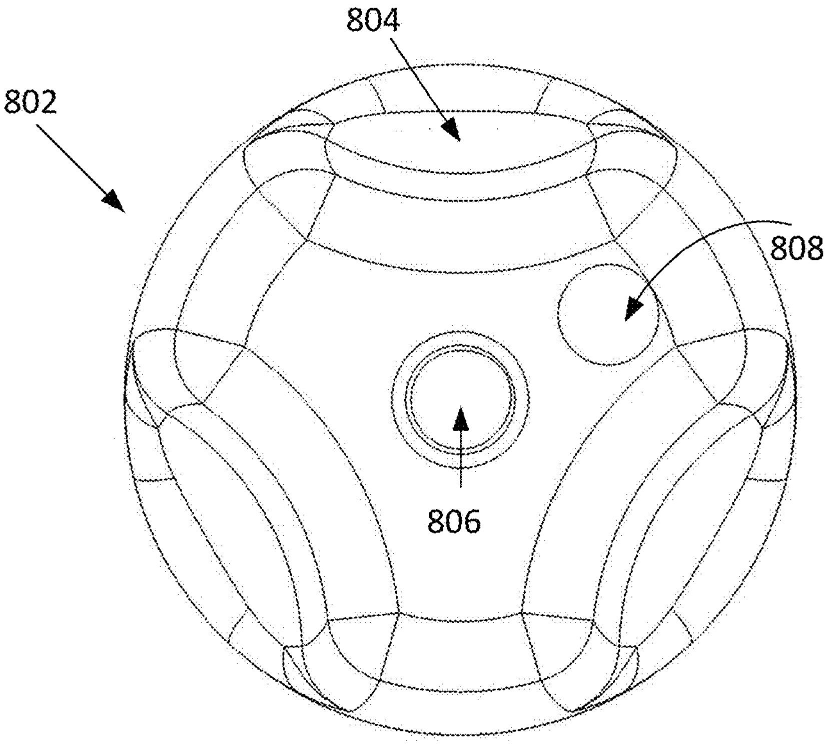
FIG. 8A illustrates a cord retainer according to an embodiment of the disclosure.
Figure 8B:
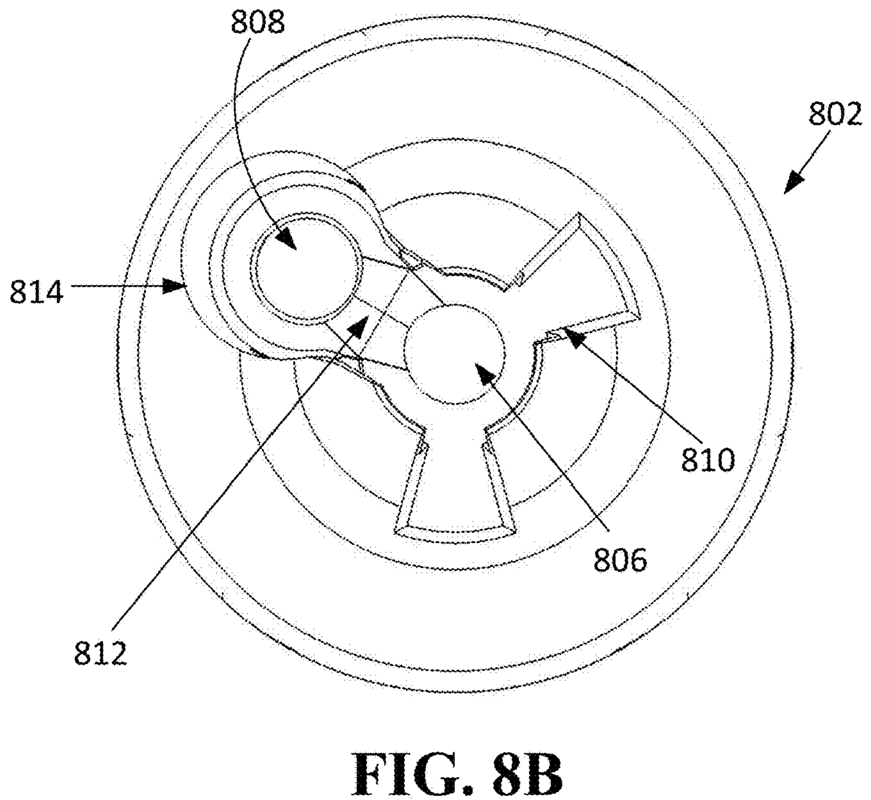
FIG. 8B illustrates a section view of the cord retainer in FIG. 8A according to an embodiment of the disclosure.

FIG. 8A illustrates a top view of a cord retainer 802 for a pullcord station according to an embodiment of the disclosure. The cord retainer 802 is shown to include a contour 804 and two openings 806 and 808 for cord (not shown) installation. FIG. 8B illustrates a bottom view of the cord retainer 802 showing a radial surface portion 810 for holding an actuator post in place and a high friction region 812 for holding the cord of the pullcord station in place. Additionally, a larger opening 814 is provided for interfacing the cord retainer 802 with an actuator post (not shown). A head end of an actuator post may fit through the larger opening 814 and then slide towards the first opening 806.

Figure 9B:
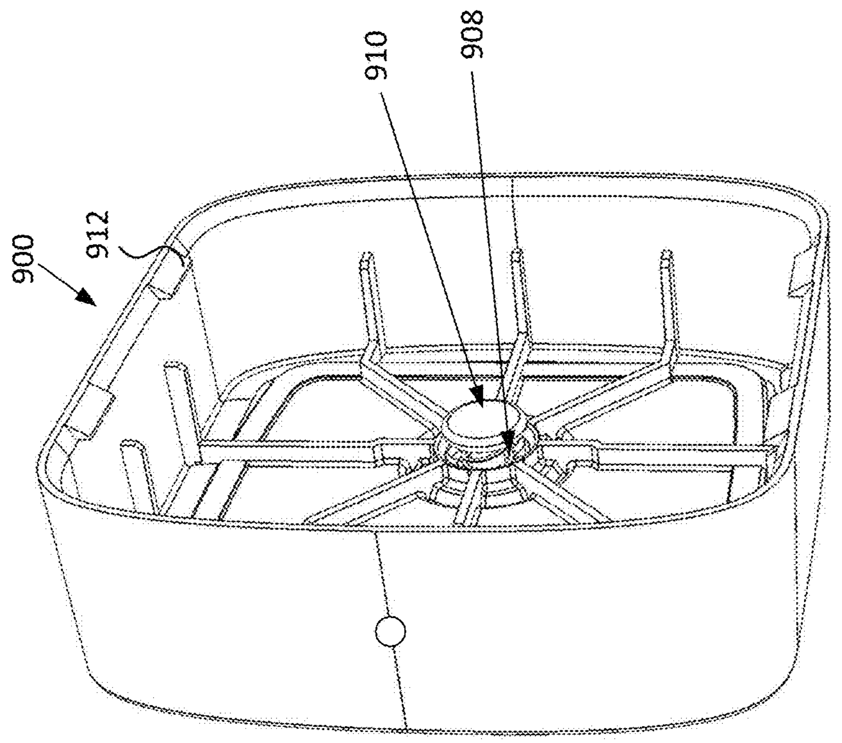
FIGS. 9A-9B illustrates perspective views of a face plate assembly according to an embodiment of the disclosure.
Figure 9A:
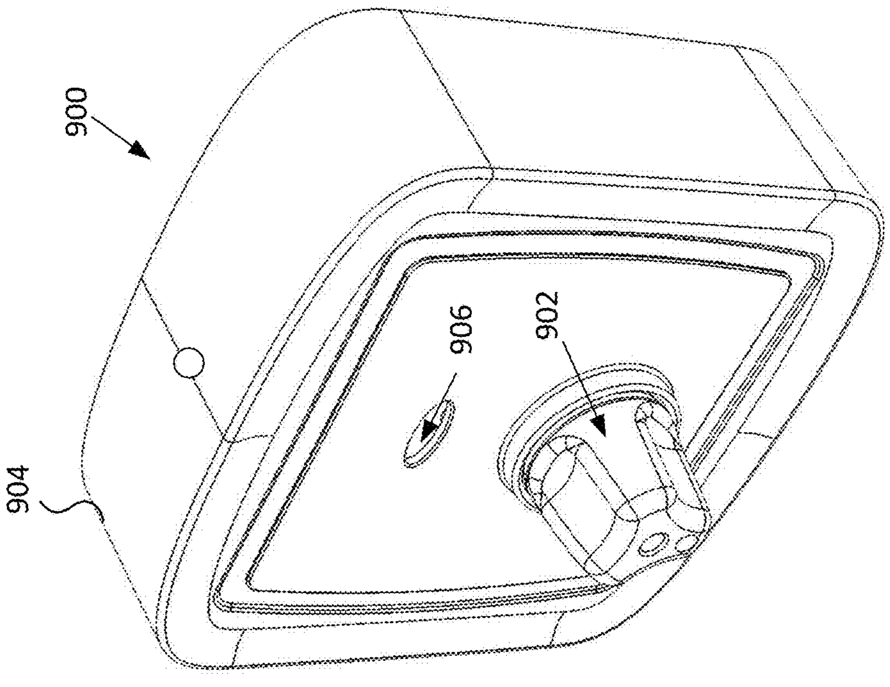

FIGS. 9A-9B illustrate perspective views of a face plate assembly 900 according to an embodiment of the disclosure. The face plate assembly 900 includes a cord retainer 902, a face plate 904, a compression spring 908, and an actuator post 910. Any cord retainer embodiment previously mentioned may be used in FIG. 9A. The face plate 904 includes one or more openings 906 that may be used for either a cancel button or an indicator light. FIG. 9A illustrates one opening 906, but it is understood that more than one opening may be provided to accommodate provision of the cancel button and the indicator light. The compression spring 908 may be provided to hold the actuator post 910 in a preferred orientation. In some embodiments, the compression spring 908 holds the actuator post 910 so that the flat end of the actuator post 910 is flush against a wall plate (not shown). The face plate 904 also includes one or more latch mechanisms that allow the face plate 904 to be secured to the wall plate without the need for using screws.

Figure 10:
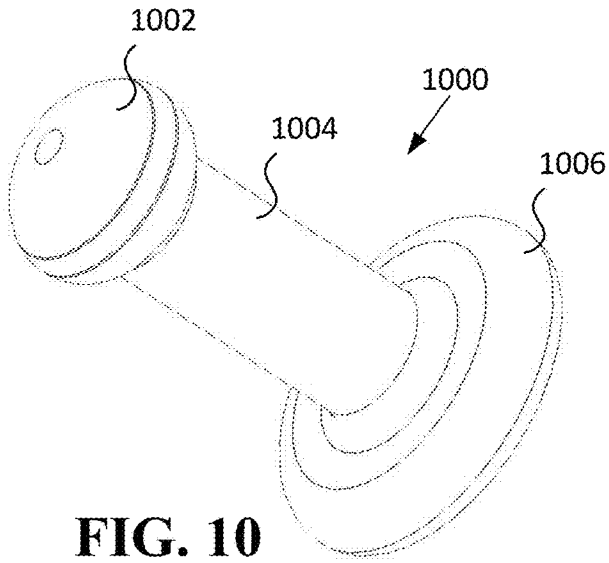
FIG. 10 illustrates an actuator post according to some embodiments of the disclosure.

FIG. 10 illustrates an actuator post 1000 according to some embodiments of the disclosure. The actuator post 1000 includes three sections: a head 1002, a stem 1004, and a bottom 1006. The head 1002 is designed to interface with a cord retainer, holding onto radial surface portions of the cord retainer. The stem 1004 may be provisioned with a compression spring. The bottom 1006 is designed to include a metalized, flat surface. In some embodiments, the bottom 1006 is the only part of the actuator post 1000 that includes metallic material while the other sections of the actuator post 1000 are made from plastic. The actuator post 1000 may be used in cord retainer embodiments of FIGS. 8B and 7B where sliding the actuator post to a locked position is desirable since the head 1002 may not be able to be compressed.

The actuator post 1000, when included in the pullcord station 300, may have a spring installed on the stem 1004. The spring is added to ensure that the actuator post 1000 returns to an original position. Since the actuator post 1000 includes metallic material in at least its bottom 1006 section, when actuated, the conductive material moves towards and away from an inductive sensor at the electronic circuit 312. One advantage to this design is that by removing mechanical pulling engaging a mechanical switch, longterm lifetime is increased. Over time, there is no wear and no bridinging due to mechanical flexing. The inductive sensing can thus have billions of operations compared to the thousands of operations of mechanical sensing. The bottom 1006 may include the flat metallized surface through a metal plating process, by adhering a metal foil to the bottom 1006 section, or having the entire actuator post 1000 constructed out of metal.

Figure 11:
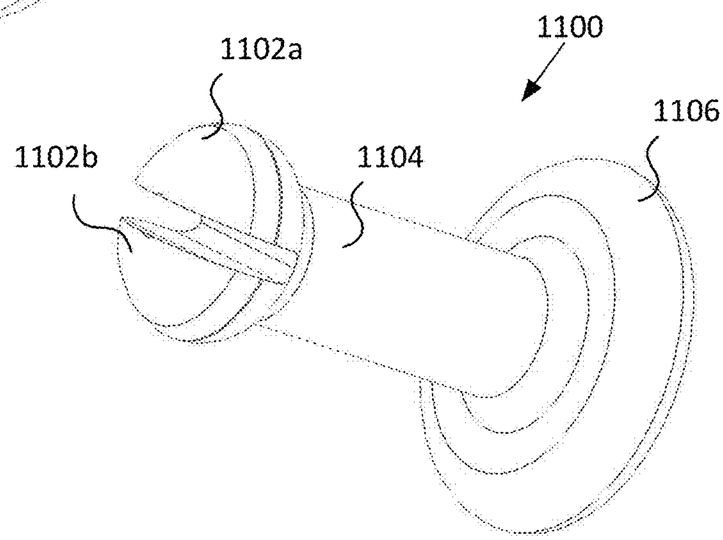
FIG. 11 illustrates another actuator post according to some embodiments of the disclosure.

FIG. 11 illustrates an actuator post 1100 according to some embodiments of the disclosure. The actuator post 1100 includes three sections: a head 1102, a stem 1104, and a bottom 1106. Compared to the embodiment of FIG. 10, the head 1102 includes two subsections 1102*a* and 1102*b*. This head design allows for the two sections 1102*a* and 1102*b* to be squeezed together thus allowing a compression of the head 1102 section of the actuator post 1100. Being able to compress the head 1102 section allows a snap-fit of the actuator post 1100 to a cord retainer. Thus, cord retainers where sliding the actuator post is not a viable option may use actuator posts with a compressible head section. The actuator post 1100 may be used with cord retainer embodiments provided in FIGS. 4-6.

Figure 12:
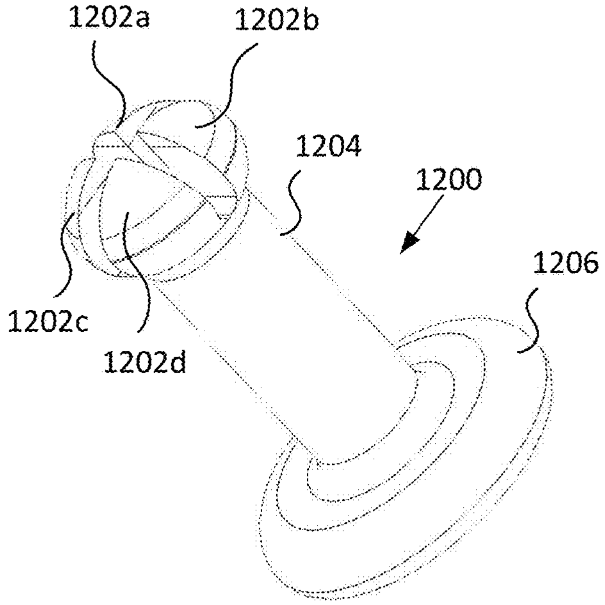
FIG. 12 illustrates yet another actuator post according to some embodiments of the disclosure.

To facilitate compression, the head section may include more than two subsections as shown in FIG. 12. The actuator post 1200 shown in FIG. 12 includes a head section 1202, a stem 1204, and a bottom 1206. The head section includes four subsections 1202*a*, 1202*b*, 1202*c*, and 1202*d*. Four subsections are provided here as an example, but the actuator post may include more than four subsections or an odd number of subsections, for example, three or five subsections. The subsections are provided to facilitate ease of compressing the head section 1202 during installation of the actuator post 1200 to a cord retainer. Smaller subsections are easier to bend than larger subsections.

Figure 13A:
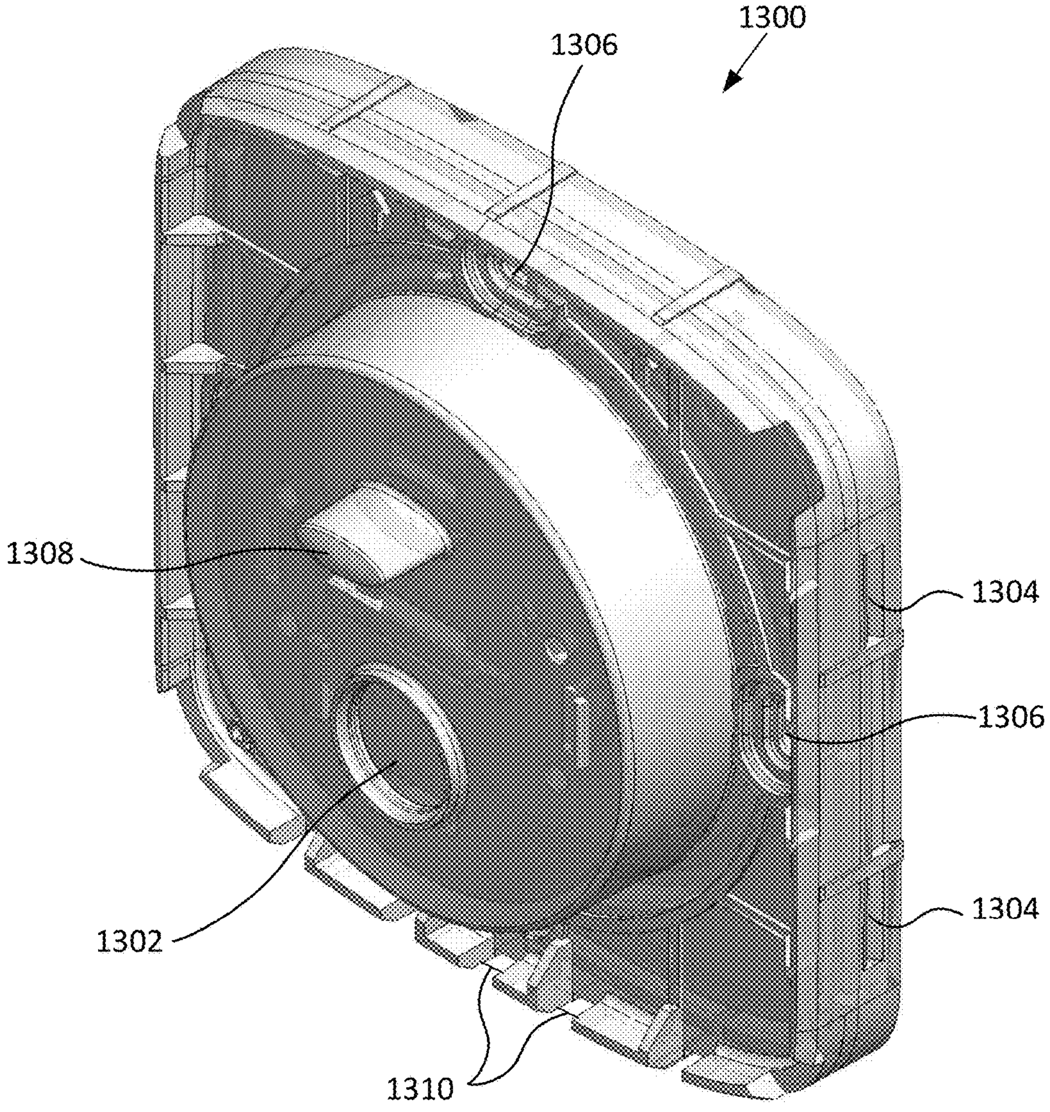
FIGS. 13A-13C illustrate several views of a wall plate according to an embodiment of the disclosure.
Figure 13B:
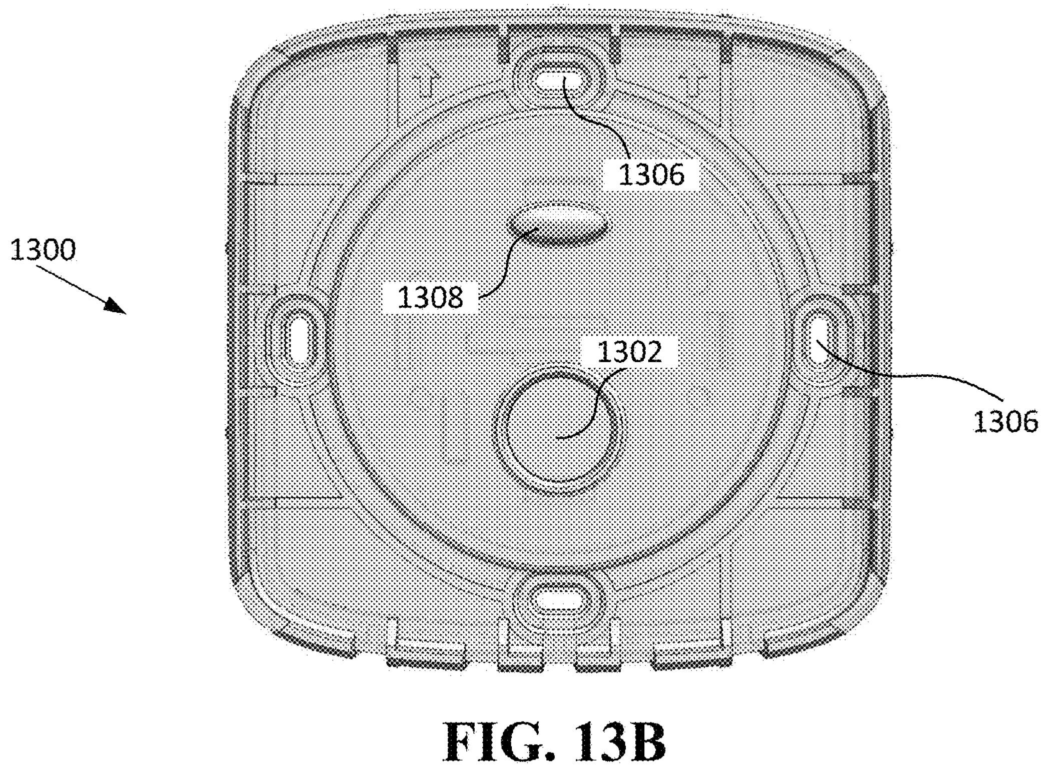
Figure 13C:
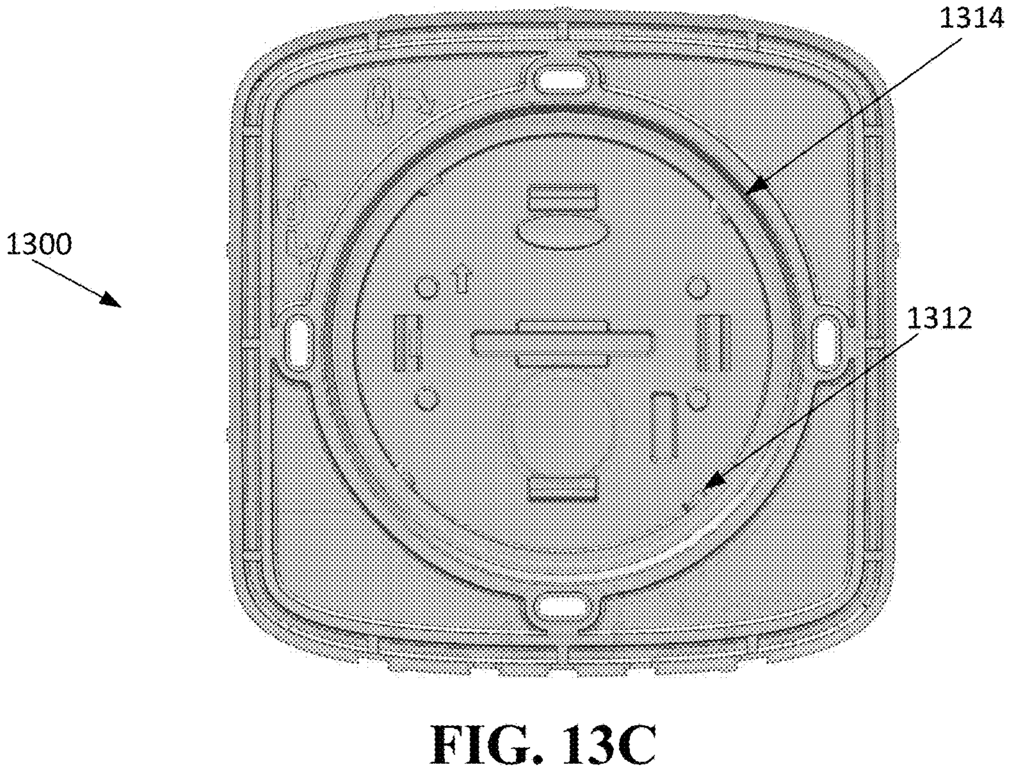

FIGS. 13A-13C illustrate several views of a wall plate 1300 according to an embodiment of the disclosure. FIG. 13A illustrates a perspective view showing an area 1302 for holding a bottom of an actuator post, female latch receptors 1304 for receiving male parts of a latch from a face plate, mounting holes 1306 to secure the wall plate 1300 to a wall, and an integrated light pipe 1308 extruded as part of the wall plate 1300 for transmission of light from a pullcord station's electronics through the cosmetic face of the pullcord station. FIG. 13B is a frontside view of the wall plate 1300, and FIG. 13C is a backside view of the wall plate 1300. The wall plate 1300 further includes protrusions 1312 for holding a back cap in place and a channel 1314 for receiving an O-ring. The frontside of the wall plate 1300 may be completely sealed with no openings allowing access to the backside of the wall plate 1300. The sealing of the frontside may be accomplished by using a single material to construct the frontside of the wall plate 1300. The wall plate 1300 may further include drainage systems for removing excess water or liquid trapped between the face plate (not shown) and the wall plate 1300. The drainage system may include holes or cutouts 1310 on the wall plate 1300 where the liquid may empty due to gravity.

Figure 14:
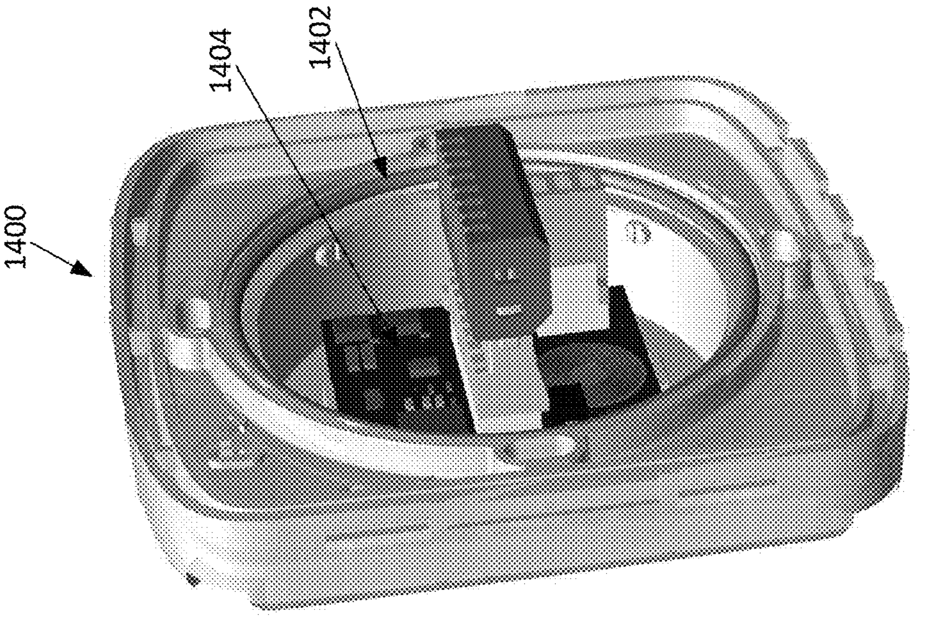
FIG. 14 illustrates a backside of a wall plate according to an embodiment of the disclosure.

FIG. 14 illustrates a backside a wall plate 1400 according to an embodiment of the disclosure. The backside of the wall plate 1400 is shown to accept an O-ring 1402 and a circuit board 1404. The circuit board 1404 is shown to sit flushed within the wall plate 1400.

Figure 15:
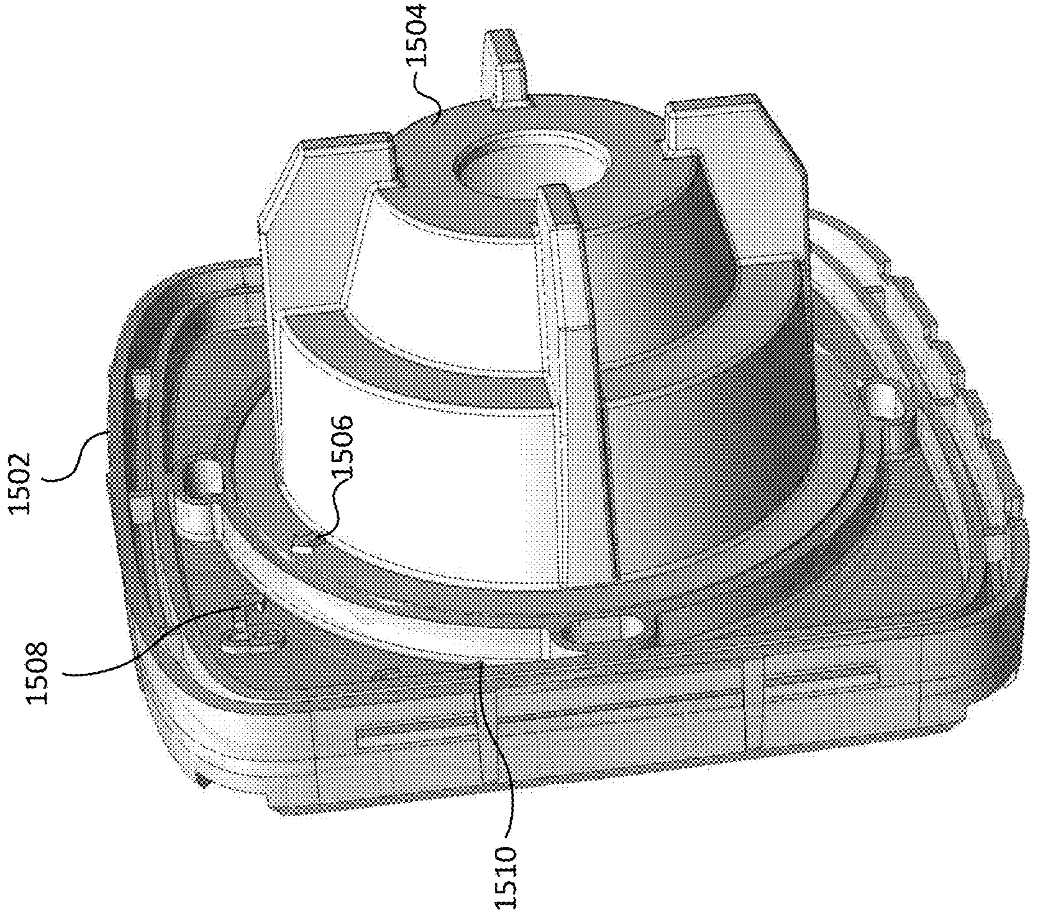
FIG. 15 illustrates a back cap in a locked position with a wall plate according to an embodiment of the disclosure.

FIG. 15 illustrates a back cap 1504 in a locked position with a wall plate 1502 according to an embodiment of the disclosure. The back cap 1504 includes an arrow indicator 1506 to help align the back cap 1504 with the wall plate 1502. The arrow indicator 1506 is aligned with one or more indicators on the wall plate 1502. For example, the arrow indicator 1506 is aligned with a lock indicator 1508 while the back cap 1504 is in a locked position with the wall plate 1502. The wall plate 1502 may also include an unlock indicator 1510 such that when the back cap 1504 is rotated so the arrow indicator 1506 is aligned with the unlock indicator 1510, the back cap 1504 is easily separated from the wall plate 1502.

Figure 16A:
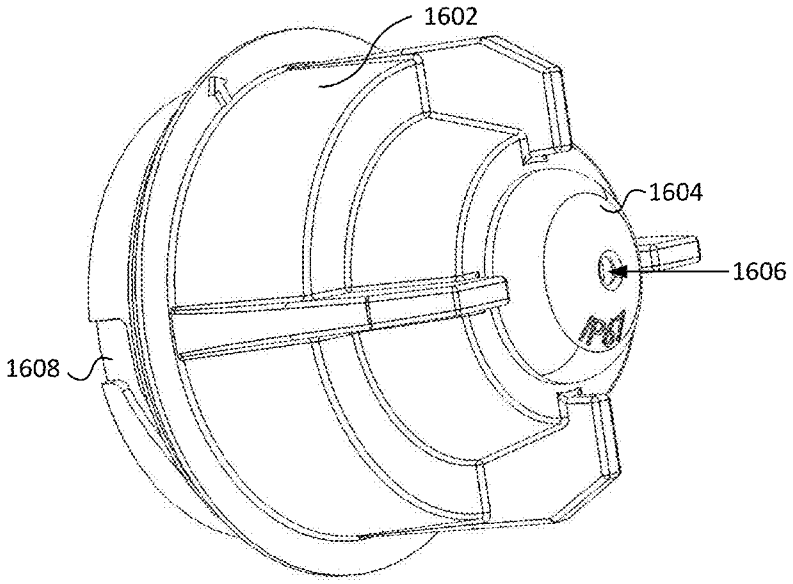
FIG. 16A illustrates a back cap with a cable grommet according to an embodiment of the disclosure.
Figure 16B:
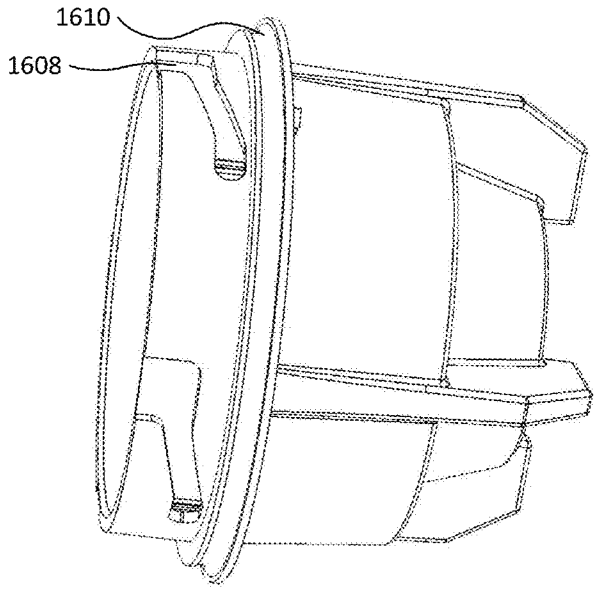
FIG. 16B illustrates a side view of the back cap of FIG. 16A according to an embodiment of the disclosure.

FIG. 16A illustrates a back cap 1602 with a cable grommet 1604 according to an embodiment of the disclosure. The cable grommet 1604 includes an opening 1606 to receive an electric cable. The back cap 1602 also includes plastic embossed channels 1608 for locking the back cap 1602 to a wall plate (not shown). The embossed channels 1608 hold the back cap 1602 to the wall plate. In addition, an O-ring channel 1610 allows an O-ring (not shown) to provide a sealing function between the back cap 1602 and the backside of the wall plate.

Figure 17:
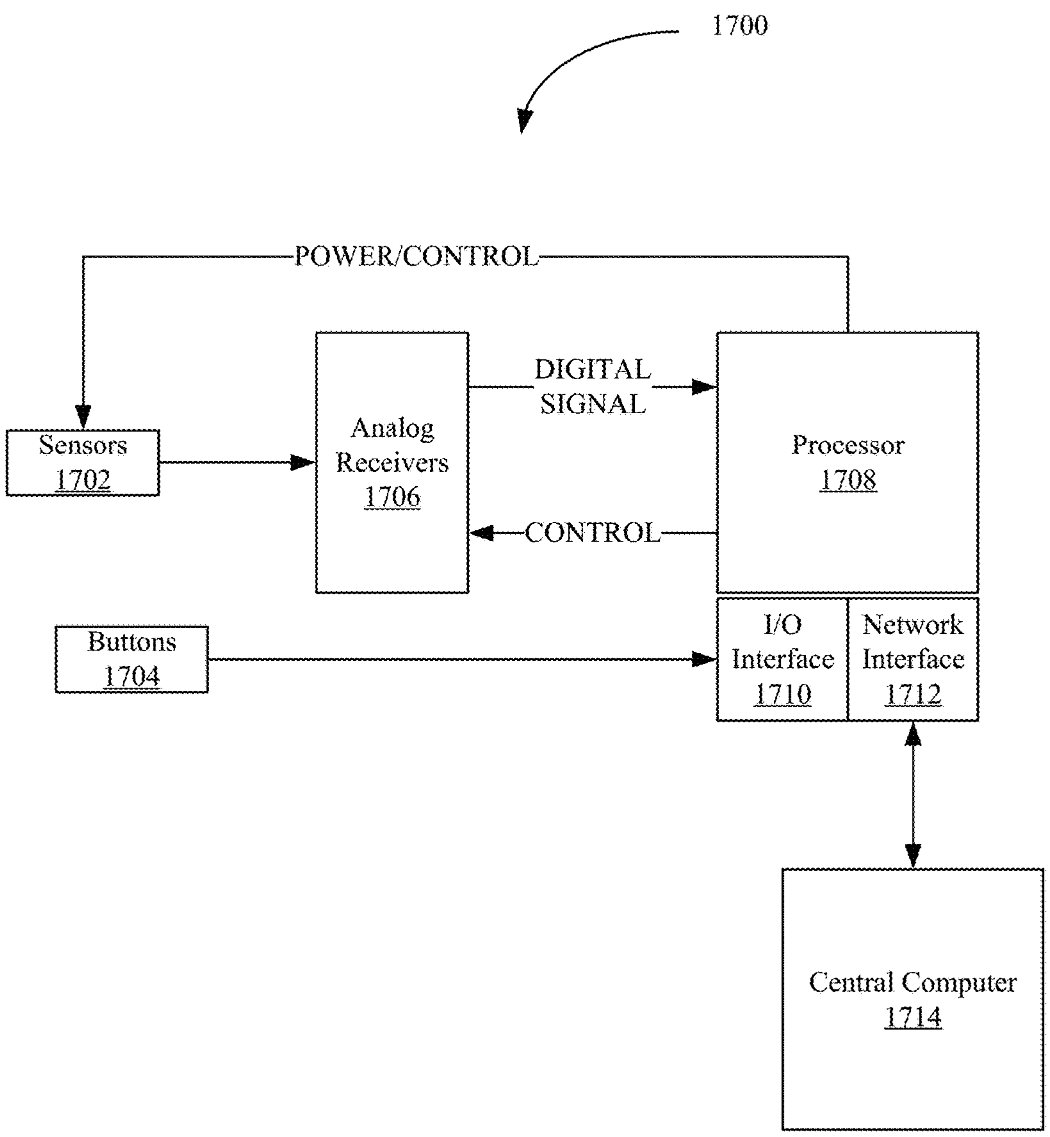
FIG. 17 illustrates an electronics architecture for a pullcord station according to some embodiments of the disclosure.

FIG. 17 illustrates an electronics architecture 1700 for processing sensor signals according to some embodiments of the disclosure. The architecture 1700 includes: one or more sensors 1702 for determining whether a cord in a pullcord station has been pulled, analog receivers 1706 for amplifying and converting sensor signals to digital signals, one or more buttons 1704 for receiving manual input, analog receivers 1706, an input/output (I/O) interface 1710 for translating button signals to voltage signals that a processor can work with, a processor 1708, a network interface 1712 for processor 1708 to communicate with outside systems, and a central computer 1714 which is an example outside system.

Sensors 1702 include, for example, inductive sensors. The analog receivers 1706 include amplifiers and analog to digital converters (ADCs) that receive analog electrical signals from the sensors 1702, amplify the analog electrical signals, and convert the analog electrical signals to digital signals in order to interface with processor 1708. The digital signals are amplified and provided to processor 1708.

Buttons 1704 include, for example, cancel button. Buttons 1704 include buttons and other switch mechanisms on the pullcord station that provide signals to the processor 1708 through the I/O interface 1710. Network interface 1712 includes hardware for transmitting and receiving information using one or more wireless or wired networks. The wired networks may include life-safety networks, for example, nurse call bus specific networks that transmit information below 38 kilobits per second (kbs). The wired networks may also include standard healthcare facility Ethernet. Wireless networks include Wi-Fi, ZigBee, 3G, 4G, Long-Term Evolution (LTE), Bluetooth®, etc.

Central computer 1714 encompasses a central system in a healthcare facility. An example of a central computer 1714 includes the nurse call server 200. Once an appropriate call level is determined, central computer 1714 coordinates with other nurse call devices 212 to alert staff in the healthcare facility of the call.

Some embodiments of the disclosure may include an additional inductive sensing call actuation mechanism to that of the actuator post in the form of a button. The button may be assembled into a retaining cavity of a faceplate of a waterproof pullcord station. The button may be realized using multiple design methodologies, but despite the methodologies, the button may include the following properties: (1) The ability to be assembled into the faceplate of the waterproof pullcord station, such that the button is able to travel towards and away from an electronic circuit with an inductive sensor, housed in the waterproof pullcord station, when pressed and released respectively; and (2) The ability to cause the inductive sensor in the electronic circuit to detect its presence and absence when moved closer and then farther away from the inductive sensor.

A button can be constructed with a single body or multiple pieces in an assembly in order to realize the aforementioned properties. In one embodiment, a bottom section of the button can be plated with a conductive material to act as an inductive sensor target, and in another embodiment, the bottom section of the button can be constructed to accept the mating and assembly of a separate inductive sensor target sub-part. This separate inductive sensor target sub-part can be a standalone plated plastic part or a solid body metallic part which is captured by a button cap section of the button. The button cap section of the button may include a surface upon which a user may press in order to create a button actuation (call or cancel) on the station.

In some embodiments, the button cap section of the button may also include mechanical elements, for example, spring mounting posts, which provide for the capture of springs. These springs provide a return force tension which causes the button to move away from the electronic circuit inductive sensor when the button is released. These springs may be located outside the range of the electronic circuit inductive sensor and are not wirelessly coupled to it.

The button cap section of the button may also include mechanical elements, for example, button alignment guides, which prevent the button from tilting more than a predetermined angle, for example, 18 degrees, out of planarity with the faceplate when being pressed and while moving towards the inductive sensor of the electronic circuit. The button cap section of the button may further include more mechanical elements, for example, button retaining snaps, which couple to the face plate button retaining cavity of the faceplate. These button retaining snaps flex and allow for assembly of the button into the faceplate. The button retaining snaps my then return to their original orientation and prevent the button from traveling beyond a designed distance away from the electronic circuit inductive sensor when the button is not being pressed. The button may be under the spring tension force pushing away from the electronic circuit inductive sensor so the button retaining snaps prevent the button from traveling beyond the distance even under this spring tension force. The button retaining snaps further prevent the button from being un-coupled from the faceplate unintentionally.

Embodiments of the disclosure provide pullcord stations meeting a waterproof standard, for example, an IP-67 rated nursecall pullcord station. The pullcord station provides water tight call placement, that is, water tight call placement throughout actuation of the cord of the pullcord station. The cord of the pullcord station can be actuatored in any direction. In some embodiments, the entire pullcord station can be submerged while retaining IP-67 level of protection.

Figure 18A:
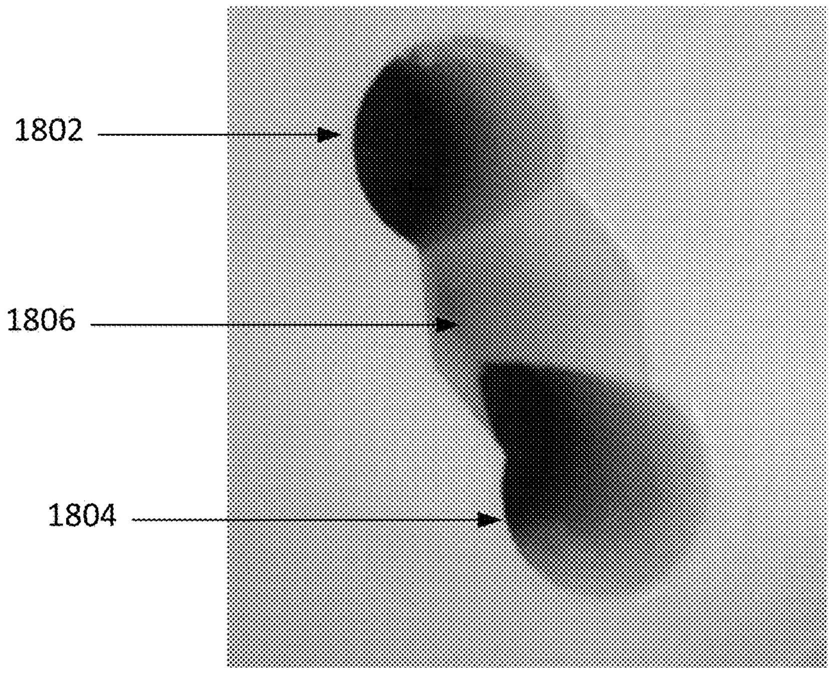
FIG. 18A provides a photograph of a 'V' shape according to an embodiment of the disclosure.
Figure 18B:
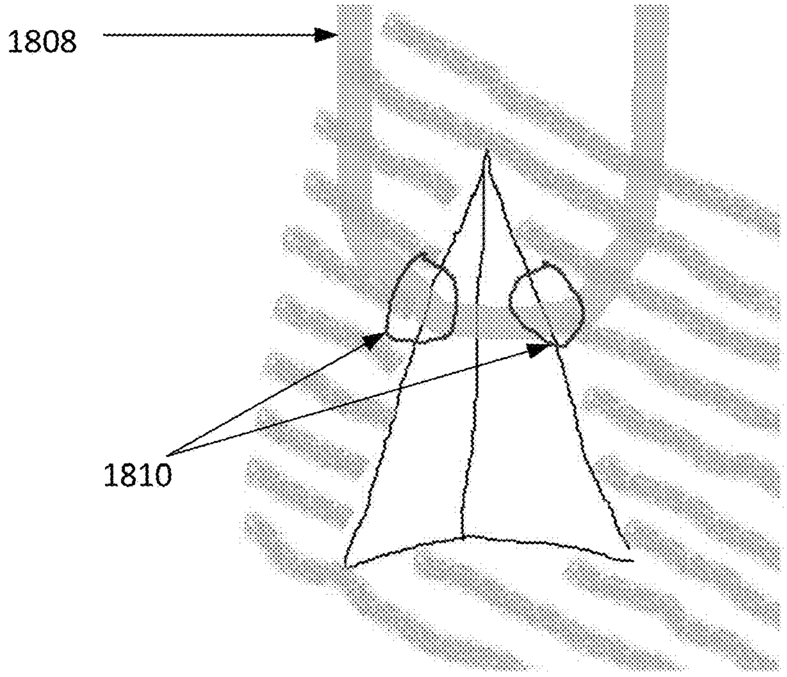
FIG. 18B provides a cross sectional sketch of a 'V' shape interfacing with a cord according to an embodiment of the disclosure.

FIG. 18A provides a photograph highlighting a 'V' shape according to an embodiment of the disclosure. Two openings 1802 and 1804 are provided on either side of the 'V' shape cavity 1806. FIG. 18B illustrates an isometric sketch of a cross-section of the 'V' shape cavity 1806. The cord 1808 interfaces with the 'V' shape cavity 1806, and the circles 1810 indicate where edges of the 'V' shape cavity "cut" into the outside of the cord. The interface between the cord 1808 and the edges of the 'V' shape cavity 1806 is such that as tension is applied to either loose end of the cord 1808, the cord 1808 is drawn progressively deeper into the 'V' shape cavity 1806, causing the cord 1808 to be pinched and thus retained. Also, the more tension that is applied on either loose end of the cord 1808, the more the cord 1808 is pinched and therefore trapped. Due to this trapping effect, subsequent pushing on the cord 1808 from a loose end does not cause the cord 1808 to easily release.

Figure 19A:
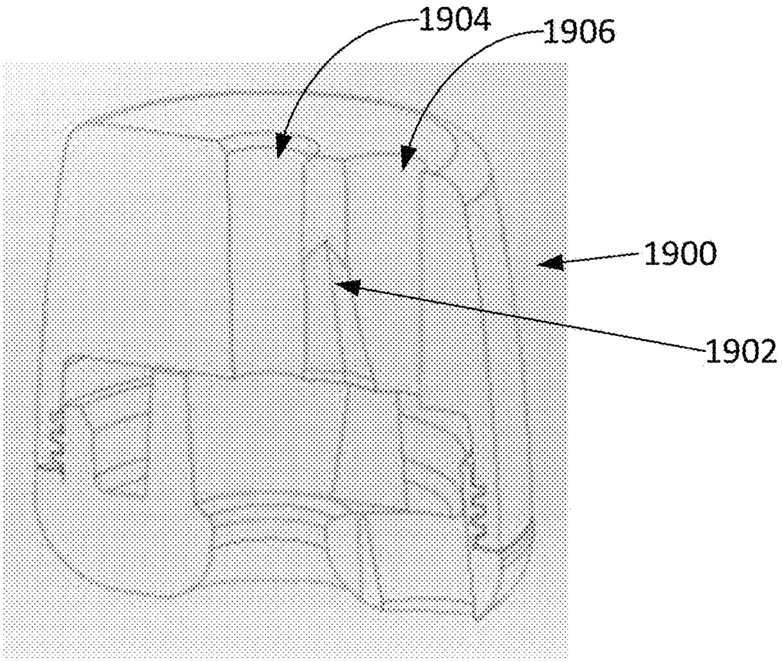
FIGS. 19A-19B illustrate various section views of a cord retainer according to some embodiments of the disclosure.
Figure 19B:
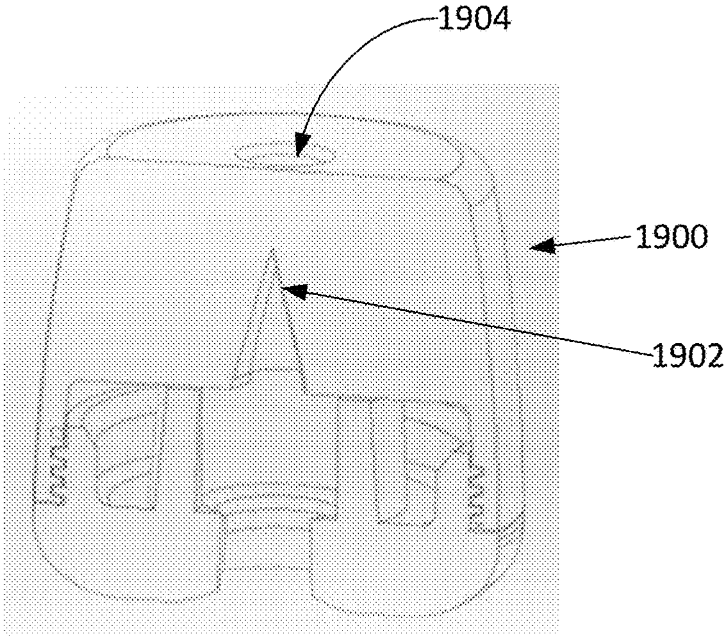
Figure 19D:
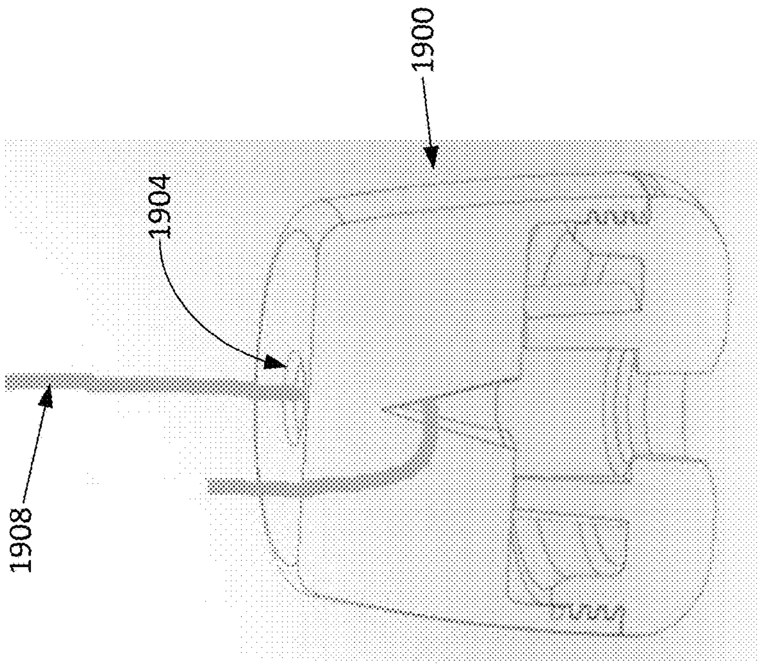
FIGS. 19C-19D illustrate various section views of a cord retainer interfacing with a cord according to an embodiment of the disclosure.
Figure 19C:
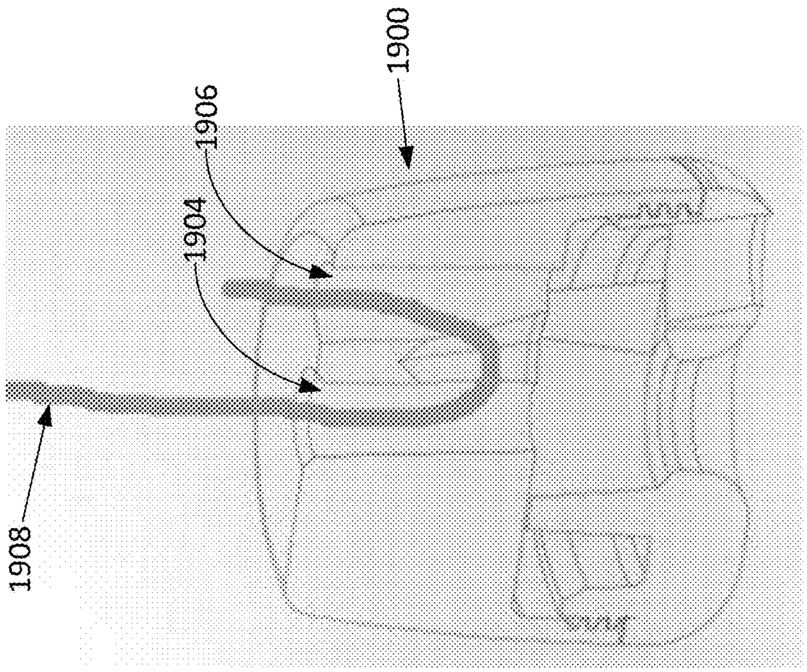

FIG. 19A illustrates a section view of a cord retainer 1900 according to some embodiments of the disclosure. FIG. 19B illustrates another section view of the cord retainer 1900. The cord retainer 1900 includes two openings 1904 and 1906 and a 'V' shape cavity 1902. A cord 1908 is shown attached to the cord retainer 1900 in FIGS. 19C-19D. The openings 1904 and 1906 receive loose ends of the cord 1908, and the cord 1908 is trapped and pinched at the edges of the 'V' shape cavity 1904.

Embodiments of the disclosure further provide a waterproof pullcord station with no flexible membranes used for cord entry. In addition, the waterproof pullcord station also has a water tight cancel button and a water tight cable connection. The pullcord station is amenable to using inexpensive components to achieve water tight cable connection. For example, off the shelf IP-67 grommet may be used for cable entry; in-line, general use, male headers pins and female connectors may be used; and cable used for the pullcord station may be field terminated, plugged and unplugged and replaced. In some embodiments, a single twist lock cap is used for inserting the circuit board during manufacturing and servicing in the field without the use of caulk or other liquid gel sealant. Standard O-rings may be used for cable seal, and adhesives or liquid sealants are not necessary to achieve the waterproof function. In some embodiments, the provision of a twist lock cap also provides assurance of a water-tight seal to ensure an installer that the back cap is secured to the wall plate. Embodiments of the disclosure further provide a waterproof pullcord station where a place of water entry is provisioned as far away from a water source as possible.

Embodiments of the disclosure further provide a water tight assurance indicator. Light transmission from inside the sealed housing may pass through the cosmetic face of the pullcord station. The circuit board disposed within the sealed housing of the pullcord station may include one or more light emitting diodes (LEDs) that emit light that travels through a light pipe provisioned in the wall plate of the pullcord station. An opening may be provided through the cosmetic face of the pullcord station to allow the emitted light to be visible to the user. The emitted light serving as the water tight assurance indicator signifying that the electronic components of the pullcord station are working properly and are not exposed to water, steam, or other liquids and/or condensation.

Embodiments of the disclosure provide a waterproof pullcord station where magnets are not used in the design. Additionally, steam will not impede call placement in the waterproof pullcord station design since inductive sensing is used rather than optical sensing. Electrical current carrying components are not exposed or accessible on the installed or sealed station. Sensing of call placement is unaffected by direct current (DC) magnetic fields.

Embodiments of the disclosure provide a waterproof pullcord station where the sealed housing opening is located on the backside of the device facing the wall on which the device is mounted. The frontside of the device on which the face plate is exposed is meant to be exposed to water and steam and is thus completely sealed with no breaks or openings. The face plate of the device is able to be removed for service and cleaning without opening the sealed housing of the waterproof pullcord station. In some cases, portions of the waterproof pullcord station which are to be exposed to water or other liquids allow for drainage and prevent retention of the water or liquid.

Embodiments of the disclosure further provide a waterproof pullcord station with a cord retainer designed to be serviceable in field without the use of specialized tools for cord replacement or station cleaning. In some cases, the cord retainer has cord locking mechanisms without the use of knots or fasteners. Thus, while in field, the cord retainer is designed to be able to lock and free the cord of the pullcord station by hand, without tools.

Embodiments of the disclosure provide a waterproof pullcord station with a cord retainer that interfaces with an actuator post, where the cord retainer and the actuator post are snapped together. A cord is attached to the cord retainer, so the cord retainer acts as an intermediary between the cord and the actuator post. Several embodiments may be constructed or envisioned for attaching the cord to the cord retainer. For example, the cord may pass through a hole in the cord retainer and then knotted to prevent the cord from slipping through the hole. In another example, a washer may be provisioned so that the cord is knotted to the washer and the washer prevents the cord from slipping through the hole. Other examples for attaching the cord to the cord retainer include using a zip tie or providing a series of holes on the cord retainer such that the cord may be woven through the holes to gain additional friction.

Embodiments of the disclosure provide a waterproof pullcord station with a cord retainer that interfaces with an actuator, with the ability for the cord retainer to lock (and unlock) with the actuator post without requiring an installer to use a tool or disassemble the pullcord station. While in use the cord retainer is pulled in various directions under various amounts of force. The cord retainer performs its intended function of transmitting those pull forces from the attached cord to the attached actuator post. The cord retainer transmits those pull forces without unlocking or disconnecting from either the attached cord or the attached actuator post. These two features, the ability to be locked and unlocked quickly and without a tool, and the ability to reliably transmit pull forces without becoming unlocked are both delivered by the design of the cord retainer.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A waterproof pullcord station for management of patient care, the pullcord station comprising:
- a cord;
- a face plate assembly comprising:
  - a cord retainer coupled to the cord, and
  - an actuator post coupled to the cord retainer; and
- a wall plate assembly comprising:
  - a wall plate comprising a frontside and a backside, wherein the frontside comprises a single material and the backside comprises an opening, the wall plate serving as a housing for an electronic circuit,
  - the electronic circuit wirelessly coupled to the actuator post and configured to determine whether the cord has been pulled by monitoring the wireless coupling between the actuator post and the electronic circuit, and
  - a back cap configured to interface with the opening of the backside;
- wherein the face plate assembly is coupled to the wall plate assembly.

2. The pullcord station according to claim 1, wherein the actuator post comprises:
- a head section configured to couple with the cord retainer; and
- a bottom section comprising a metallic surface.

3. The pullcord station according to claim 2, wherein:
- the electronic circuit comprises an inductive sensor, and the monitoring the wireless coupling between the actuator post and the electronic circuit comprises determining with the inductive sensor whether the metallic surface of the bottom section of the actuator post is moving towards or away from the inductive sensor.

4. The pullcord station according to claim 2, wherein the head section comprises two or more subsection designed to enable the head section to compress in order to couple with and decouple from the cord retainer.

5. The pullcord station according to claim 1, wherein the cord retainer comprises:
- a first opening for receiving one end of the cord;
- a high friction region for holding the cord in place; and
- a second opening for dispatching the one end of the cord;
- wherein the high friction region comprises a 'V' shape and the cord hooks around the 'V' shape to be held in place.

6. The pullcord station according to claim 1, wherein:
- the cord retainer is shaped to allow the cord to be pulled from any angle; and
- in response to the cord being pulled:
  - the electronic circuit determines through the wireless coupling between the electronic circuit and the actuator post that a position of the actuator post has changed, and
  - the electronic circuit initiates a call.

7. The pullcord station according to claim 6, wherein:
- the cord retainer is configured to act like a lever operating in 360° to move the actuator post when a side-force is produced by the cord.

8. The pullcord station according to claim 7, wherein:
- the cord retainer comprises a base with a rounded outer surface in a form of a partial toroid, the base allowing the cord retainer to smoothly change the position of the actuator post when the side-force is produced by the cord.

9. The pullcord station according to claim 1, wherein the frontside of the wall plate further comprises cutouts that allow liquid to drain from the pullcord station.

10. The pullcord station according to claim 1, wherein:
- the back cap comprises one or more embossed channels for locking the back cap to the opening of the backside of the wall plate; and
- the backside of the wall plate comprises one or more protrusions to interface with the one or more embossed channels.

11. The pullcord station according to claim 1, wherein:
- the wall plate assembly further comprises an O-ring; and
- the back cap further comprises a channel to receive the O-ring.

12. The pullcord station according to claim 1, wherein the wall plate assembly further comprises:
- a cable grommet coupled to the back cap, the cable grommet comprising an opening to receive an electrical cable;
- wherein the back cap comprises an opening to receive the cable grommet, and the cable grommet is configured to seal the opening of the back cap when the electrical cable is installed in the cable grommet.

13. The pullcord station according to claim 12, wherein the electrical cable serves as a wired communication channel between the electronic circuit and a nurse call server.

14. A system for management of patient care, the system comprising:

a nurse call server comprising a processor and a non-transitory computer readable medium; and a waterproof pullcord station comprising:

a cord;

a face plate assembly comprising:

a cord retainer coupled to the cord, and an actuator post coupled to the cord retainer; and a wall plate assembly coupled to the face place assembly, the wall plate assembly comprising:

a wall plate comprising a frontside and a backside, wherein the frontside comprises a single material and the backside comprises an opening, the wall plate serving as a housing for an electronic circuit, the electronic circuit wirelessly coupled to the actuator post and configured to determine whether the cord has been pulled by monitoring the wireless coupling between the actuator post and the electronic circuit, and a back cap configured to interface with the opening of the backside;

wherein the waterproof pullcord station initiates a call to the nurse call server when the cord has been pulled.

15. The system according to claim 14, wherein the actuator post comprises:

a head section configured to couple with the cord retainer; and a bottom section comprising a metallic surface.

16. The system according to claim 15, wherein:

the electronic circuit comprises an inductive sensor, and the monitoring the wireless coupling between the actuator post and the electronic circuit comprises determining with the inductive sensor whether the metallic surface of the bottom section of the actuator post is moving towards or away from the inductive sensor.

17. The system according to claim 14, wherein the cord retainer comprises:

a first opening for receiving one end of the cord;

a high friction region for holding the cord in place; and a second opening for dispatching the one end of the cord;

wherein the high friction region comprises a 'V' shape and the cord hooks around the 'V' shape to be held in place.

18. The system according to claim 14, wherein:

the cord retainer is shaped to allow the cord to be pulled from any angle; and in response to the cord being pulled:

the electronic circuit determines through the wireless coupling between the electronic circuit and the actuator post that a position of the actuator post has changed, and the electronic circuit initiates the call to the nurse call server.

19. The system according to claim 18, wherein:

the cord retainer is configured to act like a lever operating in 360° to move the actuator post when a side-force is produced by the cord.

20. The system according to claim 19, wherein:

the cord retainer comprises a base with a rounded outer surface in a form of a partial toroid, the base allowing the cord retainer to smoothly change the position of the actuator post when the side-force is produced by the cord.

21. A waterproof pullcord station comprising:

a cord;

a face plate assembly comprising:

a cord retainer coupled to the cord, and an actuator post coupled to the cord retainer; and a wall plate assembly coupled to the face plate assembly, the wall plate assembly comprising:

a wall plate comprising a frontside and a backside, wherein the frontside comprises a single material and the backside comprises an opening, and a back cap configured to interface with the opening of the backside to seal the backside creating an interior cavity with the backside;

wherein the face plate assembly is configured to allow excess liquid to drain from the pullcord station, and the wall plate assembly is configured to prevent ingress of water in the interior cavity.

* * * * *